(12) United States Patent
Zurbriggen et al.

(10) Patent No.: US 8,715,698 B2
(45) Date of Patent: May 6, 2014

(54) TRUNCATED SECRETORY ASPARTYL PROTEINASE 2

(75) Inventors: Rinaldo Zurbriggen, Schmitten (CH); Flavia de Bernardis, Rome (IT); Antonio Cassone, Rome (IT); Silvia Rasi, Bern (CH)

(73) Assignees: Pevion Biotech, AG, Ittlingen (CH); Istituto Superiore di Sanita, Rome (IT)

( * ) Notice: Subject to any disclaimer, the term of this patent is extended or adjusted under 35 U.S.C. 154(b) by 544 days.

(21) Appl. No.: 12/678,692

(22) PCT Filed: Sep. 19, 2008

(86) PCT No.: PCT/EP2008/007920
§ 371 (c)(1),
(2), (4) Date: Jul. 6, 2010

(87) PCT Pub. No.: WO2009/036997
PCT Pub. Date: Mar. 26, 2009

(65) Prior Publication Data
US 2010/0285109 A1    Nov. 11, 2010

(30) Foreign Application Priority Data
Sep. 19, 2007 (EP) .................. 07018420

(51) Int. Cl.
*A61K 39/00* (2006.01)
*C07K 1/00* (2006.01)
*A61K 38/00* (2006.01)

(52) U.S. Cl.
USPC .............. 424/274.1; 424/185.1; 424/184.1; 530/350; 530/823; 514/1.1; 435/975

(58) Field of Classification Search
CPC ............ A61K 2300/00; A61K 31/185; A61K 2039/505; C07K 14/40; C12Q 1/37
See application file for complete search history.

(56) References Cited

U.S. PATENT DOCUMENTS

| | | |
|---|---|---|
| 6,747,137 B1 | 6/2004 | Weinstock et al. |
| 7,241,613 B1 | 7/2007 | Willins et al. |

FOREIGN PATENT DOCUMENTS

| | | |
|---|---|---|
| EP | 0 468 812 | 1/1992 |
| JP | 2002 078494 | 3/2002 |

OTHER PUBLICATIONS

Greenspan et al. (Nature Biotechnology 7: 936-937, 1999.*
Altschul, et al., "Gapped BLAST and PSI-BLAST: a new generation of protein database search programs," *Nucleic Acids Research*, 1997, vol. 25, No. 17, pp. 3389-3402.
Altschul, et al., "Basic Local Alignment Search Tool," *J. Mol. Biol.*, 1990, 215, pp. 403-410.
Böttcher, et al., "Short Communications—A rapid and sensitive submicro phosphorus determination," *Anal. Chim. Acta*, 24 (1961)m oo, 203-204.
Ball, "Quantitation of Proteins by Elution of Coomassie Brilliant Blue R from Stained Bands after Sodium Dodecyl Sulfate—Polyacrylamide Gel Electrophoresis," *Analytical Biochemistry*, 155, 1986, pp. 23-27.
Cassone, et al., "Rats Clearing a Vaginal Infection by *Candida albicans* Acquire Specific, Antibody-Mediated Resistance to Vaginal Reinfection," *Infection and Immunity*, Jul. 1995, vol. 63, No. 7, pp. 2619-2624.
De Bernardis, et al., "Protective Role of Antimannan and Anti-Aspartyl Proteinase Antibodies in an Experimental Model of *Candida albicans* Vaginitis in Rats," *Infection and Immunity*, Aug. 1997, vol. 65, No. 8, pp. 3399-3405.
De Bernardis, et al., "Intravaginal and Intranasal Immunizations Are Equally Effective in Inducing Vaginal Antibodies and Conferring Protection against Vaginal Candidiasis," *Infection and Immunity*, May 2002, vol. 70, No. 5, pp. 2725-2729.
De Bernardis, et al., "Local Anticandidal Immune Responses in Rat Model of Vaginal Infection by and Protection against *Candida albicans*," *Infection and Immunity*, Jun. 2002, vol. 68, No. 6, pp. 3297-3304.
Gerhard, "The Analysis of the Monoclonal Immune Response to Influenza Virus—II. The Antigenicity of the Viral Hemagglutinin," *The Journal of Experimental Medicine*, vol. 144. 1976, pp. 985-995.
Glück, "Adjuvant activity of immunopotentiating reconstituted influenza virosomes (IRIVs)," *Vaccine* 17 (1999), pp. 1782-1787.
Hochuli, et al., "Genetic Approach to Facilitate Purification of Recombinant Proteins With A Novel Metal Chelate Adsorbent," *Bio/Technology*, Nov. 1988, pp. 1321-1325.
Kumar, et al., ""Universal" T Helper Cell Determinants Enhance Immunogenicity of a *Plasmodium falciparum* Merozoite Surface Antigen Peptide," *The Journal of Immunology*, vol. 148, No. 5, Mar. 1992, pp. 1499-1505.
LaValle, et al., "Molecular Cloning and Expression of a 70-Kilodalton Heat Shock Protein of *Candida albicans*," *Infections and Immunity*, Oct. 1995, vol. 63, No. 10, pp. 4039-4045.
Moreno, et al., "CD4+ T Cell Clones Obtained from *Plasmodium falciparum* Sporozoite-Immunized Volunteers Recognize Polymorphic Sequences of the Circumsporozoite Protein[1]," *The Journal of Immunology*, vol. 151, No. 1, Jul. 1993, pp. 489-499.
Naglik, et al., "In Vivo Analysis of Secreted Aspartyl Proteinase Expression in Human Oral Candidasis," *Infection and Immunity*, May 1999, vol. 67, No. 5, pp. 2482-2490.
Nyirjesy, "Chronic Vulvovaginal Candidiasis," *American Family Physician*, Feb. 2001, vol. 63, No. 4, pp. 697-702.

(Continued)

*Primary Examiner* — S. Devi
(74) *Attorney, Agent, or Firm* — Saul Ewing, LLP

(57) ABSTRACT

The present invention relates to an isolated truncated form of the secretory aspartyl proteinase 2, as well as to nucleic acid molecules encoding same. The present invention also relates to a composition comprising an isolated truncated form of the secretory aspartyl proteinase 2, as well as to nucleic acid molecules encoding same.

11 Claims, 7 Drawing Sheets

(56) References Cited

OTHER PUBLICATIONS

Pöltl-Frank, et al., "Use of reconstituted influenza virus virosomes as an immunopotentiating delivery system for a peptide-based vaccine," *Clin Exp Immunol*, 1999, 117:496-503.

Schaller, et al., "The Secreted Aspartyl Proteinases Sap1 and Sap2 Cause Tissue Damage in an In Vitro Model of Vaginal Candidiasis Based on Reconstituted Human Vaginal Epithelium," *Infection and Immunity*, Jun. 2003, vol. 71, No. 6, pp. 3227-3234.

Schaller, et al., "Invasion of *Candida albicans* Correlates with Expression of Secreted Aspartic Proteinases during Experimental Infection of Human Epidermis," *J Invest Dermatol*, 114:712-717, 2000.

Skehel, et al., "The Polypeptide Composition of Influenza A Viruses," *Virology*, 44, 1971, pp. 396-408.

Abad-Zapatero et al., "Structure of a secreted aspartic protease from *C. albicans* complexed with a potent inhibitor: Implications for the design of antifungal agents", Protein Science, 1996, pp. 640-652.

Vilanova et al., "Protection against systemic candidiasis in mice immunized with secreted aspartic proteinase 2", Immunology, 2004, pp. 334-342.

Bernardis et al., "Human Domain Antibodies against Virulence Traits of *Candida albicans* Inhibit Fungus Adherence to Vaginal Epithelium and Protect against Experimental Vaginal Candidiasis", Anticandidal Domain Antibodies, Jan. 2007, pp. 149-157.

Accession No. XP-002470367, printed Feb. 25, 2008.

Accession No. XP-002470495, printed Feb. 22, 2008.

Cutfield, et al., "Chain A, Secreted Aspartic Proteinase (Sap2) From *Candida albicans* Complexed With A70450," PDB accession number: 1EAG_A, online: http://www.ncbi.nlm.nih.gov/protein/1EAG_A, 2012.

* cited by examiner

A. tSap2

B. wtSap2

C. tSap2: Western Blot using anti-Sap2

VAGINAL COLONIZATION WITH *C.ALBICANS* IN RATS INTRAVAGINALLY TREATED WITH MAb

TRUNCATED SECRETORY ASPARTYL PROTEINASE 2

CROSS-REFERENCE TO RELATED APPLICATION

The present application is a 35 U.S.C. §371 national phase application from, and claiming priority to, International Application No. PCT/EP2008/007920, filed Sep. 19, 2008, and published under PCT Article 21(2) in English, which claims priority to European Application No. 07018420.5, filed Sep. 19, 2007, which applications are incorporated by reference herein in their entireties.

FIELD OF THE INVENTION

The present invention relates to a truncated form of the secretory aspartyl proteinase 2 (Sap2), as well as to nucleic acid molecules encoding same. This truncated Sap2 polypeptide (tSap2) is surprisingly stable, has full immunogenicity upon intravaginal administration and confers full protection against intravaginal challenge by the Candida fungus. The present invention further relates to compositions comprising tSap2 and to the use of tSap2 in the preparation of such compositions.

BACKGROUND OF THE INVENTION

Infections caused by Candida albicans and other related fungal species continue to have a sustained prevalence worldwide (Nyirijesy American Family Physician (2001) 63:697-702). The wide spectrum of candidiasis and its recognized clinical importance has stimulated interest in understanding the various fungal and host components involved in the pathogenesis of these diseases. C. albicans is a human commensal and its interaction with the host immune system plays an important role both in the commensalism and in controlling the infection. Several potential antigenic targets of the host response against C. albicans have been investigated with the ultimate aim to generate immunological tools to fight candidiasis. The most investigated antigenic targets include mannoproteins (MP), some with adhesive or receptor-like functions, heat shock proteins, enolase and secretory aspartyl proteinases (Sap) (Schaller et. al., J. of Invet. Dermatology (2000) 114: 712-717). Together with recent advances in the mechanisms of anti-candidal immune responses, these studies have laid the groundwork for further investigations into the selected use of some of the above targets as potential therapeutic or preventive vaccines or for producing antibodies for passive vaccination.

It has previously been found that expression of a member of the Sap family of C. albicans, Sap2, is critically required for infection, and that intravaginal or even intranasal immunization with full-length wild type Sap2 conferred an elevated degree of protection against Candida infection (de Bernardis, Infect and 1 mm. (2002) 70, 2725-2729). However, wild type Sap2 protein was shown to be enzymatically active, very unstable, and endowed with toxicity potential (Schaller et al, Infect and Imm (2003), 71, 3227-3234) making it a poor choice for a vaccine.

Therefore, there is a need in the art for a Sap2 antigen that is capable of eliciting efficient antibody and cellular immune responses against C. albicans without having the drawbacks of the full-length wild type Sap2 associated thereto.

SUMMARY OF THE INVENTION

The present invention fulfils this need by the provision of a truncated Sap2 polypeptide (tSap2). The tSAP2 according to the present invention, is surprisingly stable, has a strong immunogenicity upon intravaginal administration and confers full protection against intravaginal challenge by the Candida fungus.

In a first aspect, the invention relates to a polypeptide comprising any of the following amino acid sequences:
  (a) the amino acid sequence shown in SEQ ID NO:1;
  (b) an amino acid sequence having a sequence identity of at least 80% with the amino acid sequence shown in SEQ ID NO:1 over the entire length of SEQ ID NO:1, wherein said amino acid sequence encodes a polypeptide that is functionally equivalent to the polypeptide having the amino acid sequence shown in SEQ ID NO:1;
  (c) an amino acid sequence encoded by a polynucleotide sequence hybridizing to the complementary sequence of SEQ ID NO:2 under highly stringent conditions, wherein said amino acid sequence is at least 15 amino acids in length, and wherein said amino acid sequence encodes a polypeptide that is functionally equivalent to the polypeptide having the amino acid sequence shown in SEQ ID NO:1;
  (d) an amino acid sequence which is a fragment of the amino acid sequence shown in SEQ ID NO:1, wherein said amino acid sequence is at least 15 amino acids in length, and wherein said amino acid sequence encodes a polypeptide that is functionally equivalent to the polypeptide having the amino acid sequence shown in SEQ ID NO:1;
wherein the polypeptide comprising any of the amino acid sequences of (a)-(d) does not have the amino acid sequence shown in SEQ ID NO:3 or SEQ ID NO:7.

In a preferred embodiment, the polypeptide according to the invention has the amino acid sequence shown in SEQ ID NO:1.

In another aspect, the invention relates to a polynucleotide comprising a nucleic acid sequence selected from the following:
  (a) the nucleic acid sequence shown in SEQ ID NO:2;
  (b) a nucleic acid sequence which is complementary to the sequence of (a);
  (c) a nucleic acid sequence which encodes the amino acid sequence shown in SEQ ID NO:1;
  (d) a nucleic acid sequence having a sequence identity of at least 80% with the sequence shown in SEQ ID NO:2 over the entire length of SEQ ID NO:2, wherein said nucleic acid sequence encodes a polypeptide that is functionally equivalent to the polypeptide having the amino acid sequence shown in SEQ ID NO:1;
  (e) a nucleic acid sequence hybridizing to the sequence of (b) under highly stringent conditions, wherein said nucleic acid sequence is at least 45 nucleotides in length, and wherein said nucleic acid sequence encodes a polypeptide that is functionally equivalent to the polypeptide consisting of the amino acid sequence shown in SEQ ID NO:1;
  (f) a nucleic acid sequence which is a fragment of the a nucleic acid sequence shown in SEQ ID NO:2, wherein said nucleic acid sequence is at least 45 nucleotides in length, and wherein said nucleic acid sequence encodes a polypeptide that is functionally equivalent to the polypeptide having the amino acid sequence shown in SEQ ID NO:1;
    wherein the polynucleotide does not have the sequence shown in SEQ ID NO:4 or SEQ ID NO:8.

In a preferred embodiment, the polynucleotide according to the invention has the nucleic acid sequence shown in SEQ ID NO:2.

In a further aspect, the present invention relates to a vector comprising the polynucleotide according to the invention. Moreover, the present invention relates to a host cell comprising said vector.

In another aspect, the present invention relates to a composition comprising at least one of the polypeptides according to the invention and/or at least one of the polynucleotides according to the invention. In a preferred embodiment, this composition is a vaccine composition. Further, the composition according to the invention may comprise one or more additional components selected from excipients, diluents, adjuvants, virosomes, or the like.

In yet another aspect, the present invention relates to the use of the polypeptide according to the invention as an immunogen and/or antigen. In a preferred embodiment, the polypeptide according to the invention is used in a vaccine composition. Moreover, the present invention relates to the use of at least one of the polypeptides and/or at least one of the polynucleotides according to the invention for preparing a pharmaceutical composition for the treatment or prevention of a *Candida* infection. Preferably, the *Candida* infection is an infection with *Candida albicans*.

The uses according to the invention may involve the use of one or more additional components selected from excipients, diluents, adjuvants, delivery vehicles, or the like. In a preferred embodiment, the delivery vehicle is a virosome. If a virosome is used as a delivery vehicle, the polypeptide and/or polynucleotide according to the invention may be linked to the surface of the virosome. Alternatively or additionally, the polypeptide and/or polynucleotide may be contained in the lumen of the virosome. A further alternative is the use of the polypeptide and/or polynucleotide according to the invention together with a virosome, wherein the virosome is used as a separate component.

In a preferred embodiment, the *Candida* infection is mucosal and/or systemic. In another preferred embodiment, the *Candida* infection is mucosal and the disease caused by said infection is selected from vulvovaginal or esophageal candidiasis.

In a further aspect, the present invention relates to a kit comprising at least one of the polypeptides and/or at least one of the polynucleotides according to the invention. In a preferred embodiment, the kit is for the in vitro diagnosis of a *Candida* infection. Preferably, the *Candida* infection is a *Candida albicans* infection. The kit according to the invention may further comprise a reagent for detecting complexes including the polypeptide. Preferably, the detection is effected by an assay selected from the group consisting of immunohistochemical assays, ELISA, RIA, Western blot analysis, FACS analysis, an immunofluorescence assay and a light emission immunoassay.

BRIEF DESCRIPTION OF THE DRAWINGS

FIG. 1A: SDS-PAGE of tSap2 stained with COOMASSIE BLUE at room temperature (left) and 37° C. (right). FIG. 1B: SDS-PAGE of Sap2 stained with COOMASSIE BLUE at room temperature (left) and 37° C. (right). FIG. 1C: Western Blot of tSAP2 with polyclonal anti-Sap2.

DETAILED DESCRIPTION OF THE INVENTION

Definitions

Figure 1:
FIG. 1 demonstrates that the preparation of the truncated Sap2 (tSap2) is much more stable than the enzymatically active wild type Sap2. 3 μg (for SDS-PAGE) or 0.3 μg (for Western Blot) of recombinantly expressed Sap2 and tSap2 were incubated in PBS for different lengths of time (30 min to 24 or 48 hours), either at room temperature or at 37° C. After incubation, both preparations were subjected to SDS-PAGE and stained with COOMASSIE BLUE.
Figure 1:
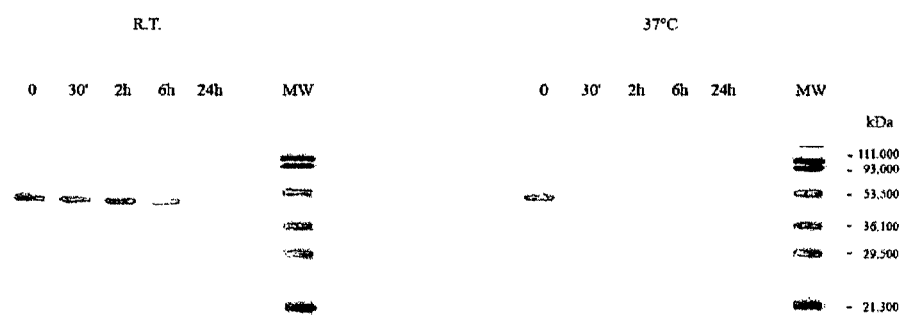
Figure 1:
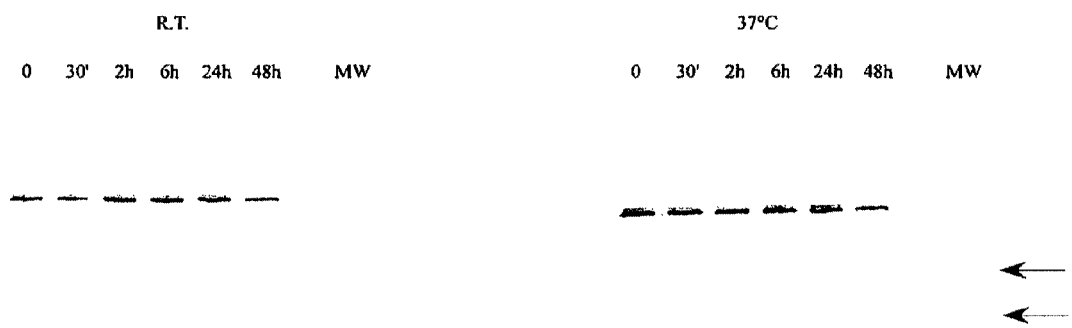

Amino acids and amino acid residues described herein may be referred to according to the accepted one or three letter code referenced in text books well known to those of skill in the art, such as Stryer, Biochemistry, 4$^{th}$ Ed., Freeman and Co., New York, 1995 and Creighton, Proteins, 2$^{nd}$ Ed. Freeman and Co., New York, 1993. As used herein, the terms "peptide" and "polypeptide" are used synonymously and in their broadest sense to refer to a molecule of two or more amino acid residues, or amino acid analogs. The amino acid residues may be linked by peptide bonds, or alternatively by other bonds, e.g. ester, ether etc. As used herein, the term "amino acid" or "amino acid residue" refers to both natural and/or unnatural or synthetic amino acids, including both the D or L enantiomeric forms, and amino acid analogs.

The terms "tSap2", "tSap2 polypeptide", and "tSap2 protein" are used interchangeably and mean a truncated form of the wild type Sap2 protein, in which the N-terminal 76 amino acids have been deleted. The terms "Sap2", "Sap2 polypeptide/protein", "wild type (wt) Sap2" and "wild type Sap2 polypeptide/protein" are used interchangeably and refer to full-length, native Sap2 such as shown in SEQ ID NO:3. Wild type Sap2 consists of 398 amino acids, of which the first 56 amino acids (1-56) code for a prepro sequence, and the remaining amino acids (57-398) code for the mature form of Sap2.

The "sequence identities" of related polypeptides and polynucleotides can be determined by means of known procedures. As a rule, special computer programs with algorithms taking account of the special requirements are used. For the purposes of the present invention, the computer program used for the determination of the identity between two sequences is BLASTP (for comparison of amino acid sequences) and BLASTN (for comparison of nucleotide sequences), as described e.g. by Altschul S et al., Nucl Acid Res 25: 3389-3402 (1997). The BLAST programs can be obtained from the National Centre for Biotechnology Information (NCBI) and from other sources (e.g. BLAST Handbook, Altschul S et al., NCB NLM NIH Bethesda Md. 20894; Altschul S et al., J. Mol. 215: 403-410 (1990)). For the purposes of the present invention, the BLASTN and BLASTP algorithm with the following default settings is used:

BLASTN
Scoring Parameters: Match/Mismatch Scores 1, −2
Gap costs: Existence: 5, Extension: 2
Filters and Masking: Low complexity regions selected
Species-specific repeats for: selected (human)
Mask for lookup table only selected
Mask lower case letters not selected
BLASTP
Scoring Parameters:
Matrix: BLOSUM62
Gap costs: Existence: 11, Extension: 1
Compositional adjustements: Composition-based statistics
Filters and Masking: None selected.
Program Advanced Options
   G Cost to open gap [Integer]
default=5 for nucleotides 11 proteins
   E Cost to extend gap [Integer]
default=2 nucleotides 1 proteins
   q Penalty for nucleotide mismatch [Integer]
default=−3
   r reward for nucleotide match [Integer]
default=1
   e expect value [Real]
default=10
   W wordsize [Integer]
default=11 nucleotides 3 proteins
   y propoff (X) for BLAST extensions in bits (default if zero)
default=20 for BLASTN 7 for other programs
   X X dropoff value for gapped alignment (in bits)
default=15 for at programs except for BLASTN for which it does not apply
   Z final X dropoff value for gapped alignment (in bits)
50 for BALSTN 25 for other programs For sequence comparison, the complete tSap2 sequences (SEQ ID NOs 1 and 2, respectively) are used as the sequence to which a related sequence is compared. Specifically, to determine the identity of a polypeptide with unknown homology to the tSap2 polypeptide according to the invention, the amino acid sequence of said first polypeptide is compared to the amino acid sequence of the tSap2 polypeptide shown in SEQ ID NO:1, over the entire length of SEQ ID NO:1. Similarly, to determine the identity of a polynucleotide with unknown homology to the tSap2 polynucleotide according to the invention, the nucleic acid sequence of said first polynucleotide is compared to the nucleic acid sequence shown in SEQ ID NO:2, over the entire length of SEQ ID NO:2.

Standard "highly stringent conditions" for hybridization are disclosed in Ausubel et al. (Eds.), Current Protocols in Molecular Biology, John Wiley & Sons (2000). Exemplary highly stringent hybridization conditions include washes with 0.1×SSC/0.1% SDS for 15 min at 68° C.

A polypeptide is considered "functionally equivalent" to the polypeptide having the amino acid sequence shown in SEQ ID NO:1 if it has essentially the same characteristics as the tSap2 polypeptide of SEQ ID NO:1. "Essentially the same characteristics" means that at least one of the properties that can be assigned to tSap2 (such as an improved stability or an increased antigenicity compared to wild type Sap2) is also displayed by the functionally equivalent polypeptide. The stability of the polypeptide can be determined by incubating the polypeptide for different time periods and then staining the polypeptide with COOMASSIE BLUE (cf. Example 1, FIG. 1). The stability is "improved" compared to the stability of the wild type Sap2 if the functionally equivalent polypeptide remains detectable for a longer time period or if it is present in larger amounts after the same time period than the wild type Sap2. The antigenicity of the polypeptide can be determined by measuring the titer of antibodies elicited by immunization of animals, such as in the rat model of vaginal Candida infection (cf. Example 4 and 5). The antigenicity is "improved" compared to the antigenicity of the wild type Sap2 if the functionally equivalent polypeptide elicits higher IgA or IgG titers than the wild type Sap2 (cf. FIG. 2).

The individual amino acids of the tSap2 polypeptide may be conservatively substituted with amino acids of equivalent size, charge and/or polarity. In addition, suitable linker, or tags (such a the HIS-tag) may be added to either end of the tSap2 polypeptide in order to facilitate their incorporation into delivery vehicles and/or their fusion to target antigens and/or to facilitate their purification and/or detection.

The term "epitope" as used herein, refers to those parts of a molecule that are recognized by T cell and/or B cell receptors. The term "antigen" is used herein to describe a molecule that binds to a T cell receptor or antibody and whose immunogenicity can be enhanced or potentiated by the adjuvants disclosed herein.

The term "adjuvant" refers to a substance distinct from target antigen that is capable of enhancing or potentiating immune effector cell activation. The term "adjuvant systems" is used herein to denote the combination of various immune-stimulatory proteins, such as the tSap2 polypeptide of the present invention, with adjuvants such as CT or HLT, to increase the immune stimulatory effect that each component of the system would exert if used by itself, as well as their combination with a suitable delivery system, such as virosomes, which may further increase the immune stimulatory effect of the compositions.

By "administration" or "administering" is meant providing one or more tSap2 polypeptides or protein-containing compositions of the invention as a drug, a pro-drug, a drug-metabolite, or a vaccine to an individual in need thereof. A vaccine is an antigenic preparation used to establish immunity to a disease. A vaccine preparation usually contains an antigen consisting of whole disease-causing organisms (killed or weakened) or parts of such organisms (e.g. the antigenic protein or DNA) and is used to confer immunity against the disease that said organisms cause. Vaccine preparations can be natural, synthetic or derived by recombinant DNA technology. Vaccines can be prophylactic (e.g. to prevent or ameliorate the effects of a future infection by any natural or "wild" pathogen), or therapeutic.

An "effective amount" is that amount of a pharmaceutical preparation that alone, or together with further doses, stimulates the desired response.

As used herein the term "virosome" refers to a vesicle produced by an in vitro procedure that is composed of lipids and at least one viral envelope protein. The lipids are either derived from a biological origin (e.g. eggs, plants, animals, cell cultures, bacteria, viruses) or produced synthetically (chemical synthesis). A virosome may be a reconstituted viral envelope which can be derived from a variety of viruses and which lacks the infectious nucleocapsids and the genetic material of the source virus, e.g. an immunopotentiating reconstituted influenza virosome (IRIV). Thus, a virosome is a special type of lipid vesicle comprising, in its lipid membrane, at least one viral envelope protein. As used herein, the term "viral envelope protein" refers to any protein encoded by an enveloped virus from which the virosome of the invention is partly or completely derived and that is present in the virosomal lipid membrane. Viral envelope proteins sometimes function as "viral fusion proteins", when they play a role in the fusion of viruses or virosomes with target cell membranes. The envelope protein(s) may be recombinant proteins, provided that the biochemical properties of the protein allow its physical attachment to a lipid membrane. These envelope proteins account for the virosomal functionality. The virosome used in the present invention may also be a chimeric virosome, meaning that it contains viral envelope proteins from at least two different virus strains. In contrast to viral systems, virosomes are safe, since the infectious nucleocapsid of the virus has been removed.

Polypeptides

The present invention provides truncated Sap2 polypeptides (tSap2) comprising any of the following amino acid sequences:
 (a) the amino acid sequence shown in SEQ ID NO:1;
 (b) an amino acid sequence having a sequence identity of at least 80% with the amino acid sequence shown in SEQ ID NO:1 over the entire length of SEQ ID NO:1, wherein said amino acid sequence encodes a polypeptide that is functionally equivalent to the polypeptide having the amino acid sequence shown in SEQ ID NO:1;
 (c) an amino acid sequence encoded by a polynucleotide sequence hybridizing to the complementary sequence of SEQ ID NO:2 under highly stringent conditions, wherein said amino acid sequence is at least 15 amino acids in length, and wherein said amino acid sequence encodes a polypeptide that is functionally equivalent to the polypeptide having the amino acid sequence shown in SEQ ID NO:1;
 (d) an amino acid sequence which is a fragment of the amino acid sequence shown in SEQ ID NO:1, wherein said amino acid sequence is at least 15 amino acids in length and wherein said amino acid sequence encodes a polypeptide that is functionally equivalent to the polypeptide having the amino acid sequence shown in SEQ ID NO:1;
 wherein the polypeptide comprising any of the amino acid sequences of (a)-(d) does not have the amino acid sequence shown in SEQ ID NO:3 or SEQ ID NO:7.

In a preferred embodiment, the polypeptide according to the invention has the amino acid sequence shown in SEQ ID NO:1.

In further preferred embodiments, the polypeptide of (b) comprises an amino acid sequence having a sequence identity of at least 85, 90, 95, 96, 97, 98, or 99% with the amino acid sequence shown in SEQ ID NO:1. Also preferred are polypeptides consisting of (having) an amino acid sequence having a sequence identity of at least 85, 90, 95, 96, 97, 98, or 99% with the amino acid sequence shown in SEQ ID NO:1.

In a preferred embodiment, the amino acid sequence of (c) and (d) has a minimum length of 20, 25, 30, 35, 40, 45, 50, 100, 150, 200, 250, or 300 amino acids.

Polynucleotides

The present invention further provides a polynucleotide coding for the truncated Sap2 polypeptide (tSap2) comprising a nucleic acid sequence selected from the following:
 (a) the nucleic acid sequence shown in SEQ ID NO:2;
 (b) a nucleic acid sequence which is complementary to the sequence of (a);
 (c) a nucleic acid sequence which encodes the amino acid sequence shown in SEQ ID NO:1;
 (d) a nucleic acid sequence having a sequence identity of at least 80% with the sequence shown in SEQ ID NO:2 over the entire length of SEQ ID NO:2, wherein said nucleic acid sequence encodes a polypeptide that is functionally equivalent to the polypeptide having the amino acid sequence shown in SEQ ID NO:1;
 (e) a nucleic acid sequence hybridizing to the sequence of (b) under highly stringent conditions, wherein said nucleic acid sequence is at least 45 nucleotides in length, and wherein said nucleic acid sequence encodes a polypeptide that is functionally equivalent to the polypeptide consisting of the amino acid sequence shown in SEQ ID NO:1;
 (f) a nucleic acid sequence which is a fragment of the a nucleic acid sequence shown in SEQ ID NO:2, wherein said nucleic acid sequence is at least 45 nucleotides in length, and wherein said nucleic acid sequence encodes a polypeptide that is functionally equivalent to the polypeptide having the amino acid sequence shown in SEQ ID NO:1;
 wherein the polynucleotide does not have the sequence shown in SEQ ID NO:4 or SEQ ID NO:8.

In a preferred embodiment, the polynucleotide according to the invention has the nucleic acid sequence shown in SEQ ID NO:2.

In further preferred embodiments, the polynucleotide comprises a nucleic acid sequence having a sequence identity of at least 85, 90, 95, 96, 97, 98, or 99% with the nucleic acid sequence shown in SEQ ID NO:2. Also preferred are polynucleotides consisting of (having) a nucleic acid sequence having a sequence identity of at least 85, 90, 95, 96, 97, 98, or 99% with the nucleic acid sequence shown in SEQ ID NO:1.

In a preferred embodiment, the nucleic acid sequence of (e) and (f) has a minimum length of 60, 75, 90, 105, 120, 135, 150, 300, 450, 600, 750, or 900 nucleotides.

In a further aspect, the present invention relates to a vector comprising the polynucleotide according to the invention. Moreover, the present invention relates to a host cell comprising said vector.

Compositions and Uses

Moreover, the present invention relates to a composition comprising at least one of the polypeptides according to the invention and/or at least one of the polynucleotides according to the invention. In a preferred embodiment, this composition is a vaccine composition. Further, the composition according to the invention may comprise one or more additional components selected from excipients, diluents, adjuvants, virosomes, or the like.

In another aspect, the present invention relates to the use of the polypeptide according to the invention as an immunogen and/or antigen. In a preferred embodiment, the polypeptide according to the invention is used in a vaccine composition. Moreover, the present invention relates to the use of at least one of the polypeptides and/or at least one of the polynucleotides according to the invention for preparing a pharmaceutical composition for the treatment or prevention of a *Candida* infection. Preferably, the *Candida* infection is an infection with *Candida albicans*.

The uses according to the invention may involve the use of one or more additional components selected from excipients, diluents, adjuvants, delivery vehicles, or the like. In a preferred embodiment, the delivery vehicle is a virosome. If a virosome is used, the polypeptide and/or polynucleotide according to the invention may be linked to the surface of the virosome. Alternatively or additionally, the polypeptide and/or polynucleotide may be contained in the lumen of the virosome. A further alternative is the use of the polypeptide and/or polynucleotide according to the invention together with a virosome, wherein the virosome is used as a separate component.

In a preferred embodiment, the *Candida* infection is mucosal and/or systemic. In another preferred embodiment, the *Candida* infection is mucosal and the disease caused by said infection is selected from vulvovaginal or esophageal candidiasis.

The present invention provides a novel peptide vaccine against candidiasis that does not carry the risk of toxic side effects associated with the use of wild type Sap2 and that shows increased stability compared to wild type Sap2, while providing powerful stimulation of immune responses against *C. albicans* infection. A truncated and stable form of Sap2 is provided which can be produced recombinantly and overcomes the well known difficulties in obtaining, purifying and standardizing the native antigen (de Bernardis, Infect and 1 mm. 2002 70, 2725-2729). Conveniently, the novel Sap2 polypeptide which lacks the first 76 amino acids of the N-terminus of the wild type form, can be produced in prokaryotic or eukaryotic cells as a recombinant product, optionally as a 6 histidine (HIS) tagged protein for the ease of purification. The truncated Sap2 polypeptide (tSap2) of the present invention is very stable. This recombinant tSap2 is highly reactive in western blots with a monoclonal antibody generated against the native Sap2, as well as with anti-Sap antibodies present in human sera of infected patients. Furthermore, monoclonal antibodies generated against the tSap2 recognize the wild type enzyme.

Figure 7:
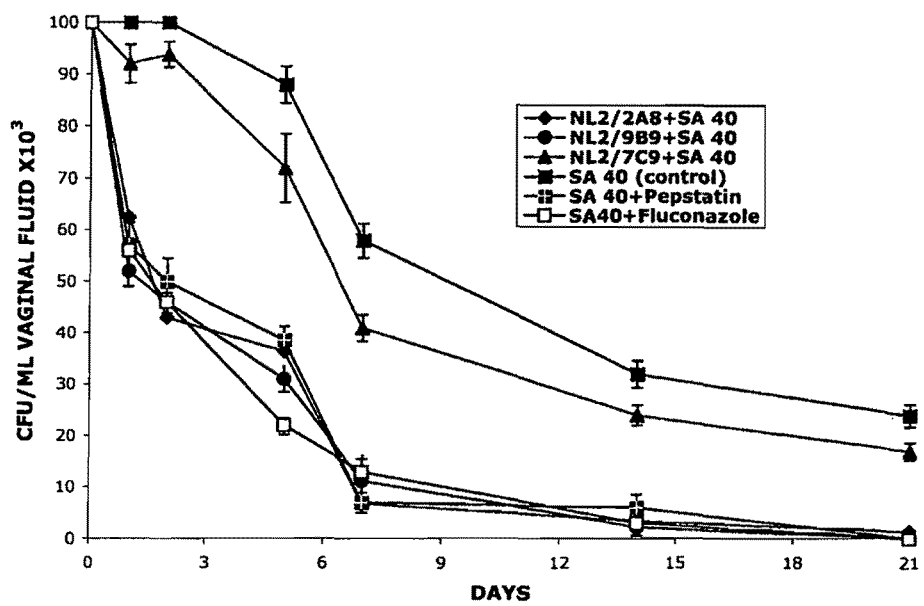
FIG. 7 shows the effect of intravaginal administration of monoclonal antibodies (mAbs) directed against tSap2 (NL2/2A8 and NL2/9b9). An isotype-matched, irrelevant antibody (anti-enolase mAb; NL2/7C9) as well as the *C. albicans* strain SA40 served as a control. The specificity of each mAb was checked by Western blotting, and all mAbs were used at identical protein concentrations in a single intravaginal administration 30 min before challenge. Both anti tSap2 mAbs (NL2/2A8 and NL2/9B9) conferred protection to rats, by inducing a very rapid clearance of fungal cells from the vagina compared to the controls, namely, rats receiving only *C. albicans* cells or the anti-enolase mAb. Under the conditions tested, the effect of anti-Sap2 mAbs was substantially comparable to that obtained with fluconazole, a popular antifungal drug, or with pepstatin, a well-known Sap inhibitor.

Immunization with tSap2 confers antibody-mediated protection against *C. albicans* infection in an experimental model of rat vaginitis. The present invention shows that monoclonal antibodies directed to the tSap2 polypeptide provide passive protection against the vaginal challenge by the fungus (FIG. 7). Thus, the present invention provides novel tools for active and passive protection against a very common, frequently chronic and sometimes antimycotic-refractory infection in women.

To further potentiate the immune stimulatory effect of the tSap2 polypeptide of the present invention, the compositions may comprise tSap2 polypeptide and one or more adjuvants.

Alternatively, the tSap2 polypeptide can be coupled to the surface of delivery vehicles, such as virosomes, by the methods disclosed herein. Alternatively, the tSap2 polypeptide may be encapsulated in delivery vehicles by methods disclosed herein. As an alternative, the tSap2 polypeptide can be both encapsulated by and linked to the surface of the delivery vehicles. Furthermore, the composition comprising tSap2 polypeptide coupled to or encapsulated in or encapsulated by and linked to the surface of the delivery vehicle may additionally contain one or more adjuvant.

The adjuvant may be selected from Freund's adjuvans (complete and incomplete), mycobacteria such as BCG, *M. vaccae*, or *Corynebacterium parvum*, Cholera toxin or tetanus toxin, *E. coli* heat-labile toxin, quil-saponin mixtures such as QS-21 (SmithKline Beecham), MF59 (Chiron) and various oil/water emulsions (e.g. IDEC-AF), MALP-2, ISCOMs. Other adjuvants which may be used include, but are not limited to: mineral salts or mineral gels such as aluminium hydroxide, aluminium phosphate, and calcium phosphate; surface active substances such as lysolecithin, pluronic polyols, polyanions, peptides, keyhole limpet hemocyanins, and dinitrophenol, immunostimulatory molecules, such as saponins, muramyl dipeptides and tripeptide derivatives, short nucleic acid stretches such as CpG dinucleotides, CpG oligonucleotides, monophosphoryl Lipid A, and polyphosphazenes, particulate and microparticulate adjuvants, such as emulsions, liposomes, virosomes, cochleates, or immunostimulating complex adjuvants. Cytokines are also useful due to their lymphocyte stimulatory properties. Many cytokines useful for such purposes will be known to one of ordinary skill in the art, including interleukin-2 (IL-2), IL-12, GM-CSF and many others. Furthermore ligands from the chemokine family, such as RANTES, a lipoprotein, a lipopeptide, a yeast cell wall component, a double-stranded RNA, a bacterial cell-surface lipopolysaccharide (LPS), flagellin, a U-rich single-stranded viral RNA, a suppressor 6f cytokine signalling small interfering RNA (SOCS siRNA), a Pan DR epitope (PADRE) and mixtures thereof are suitable.

The tSap2 polypeptide of the present invention may be produced by chemical synthesis, or it may be of recombinant origin. The tSap2 polypeptide may be recombinantly produced using a nucleic acid molecule encoding the protein. In addition, its sequence may be modified as long as it retains the ability to stimulate the immune responses to *C. albicans* disclosed herein.

Moreover, the invention embraces functional variants of the tSap2 polypeptide. As used herein, a "functional variant" or "variant" of the tSap2 polypeptide is a protein which contains one or more modifications to the primary amino acid sequence of the immunostimulatory tSap2 polypeptide while retaining the immunostimulatory effect disclosed herein. If a functional variant of the tSap2 polypeptide involves an amino acid substitution, conservative amino acid substitutions typically will be preferred, i.e. substitutions which retain a property of the original amino acid such as charge, hydrophobicity, conformation, etc. Examples of conservative substitutions of amino acids include substitutions made among amino acids within the following groups: (1) M, I, L, V; (2) F, Y, W; (3) K, R, H; (4) A, G; (5) S, T; (6) Q, N; and (7) E, D.

Modifications which generate functional variants of the tSap2 polypeptide may be made in order to enhance protein stability in an expression system, to enhance the stability of protein-protein binding such as HLA-peptide binding, or to increase the avidity of immune receptors. Any method for preparing modified or variant proteins can be employed, such as synthesis of the modified or variant protein or its recombinant production using a mutated nucleic acid molecule.

The identification of additional or optimized immunostimulatory tSap2 polypeptides may also include the step of comparing the stimulation of T or B cells by the tSap2 polypeptide and the stimulation of T or B cells by the functional variant as a determination of the effectiveness of the stimulation of immune effector cells by the functional variant. By comparing the functional variant tSap2 polypeptide with a known tSap2 polypeptide, proteins with increased immune cell stimulatory properties can be prepared.

The individual tSap2 polypeptide may also have one or more amino acids added to either or both ends. Thus, for example, linker or spacer amino acids may be added to the N- or C-terminus of the protein or both, to allow for convenient coupling of the peptides to a delivery vehicle such as a virosome. In some instances, it may be desirable to add a histidine tag to the tSap2 polypeptide, for ease of experimental purification and/or manipulation.

The present invention also demonstrates that the combination of virosomes as human compatible immunopotentiating delivery agents with the tSap2 polypeptide of the present invention potentiates the generation of efficient immune responses against candidiasis. Thus, the invention provides a novel tSap2 polypeptide the immunogenic efficacy of which can be further enhanced by its combination with an immunopotentiating delivery system and/or one or more adjuvant(s). While immunopotentiating reconstituted influenza virosomes (IRIVs) are well suited, a number of other delivery vehicles, such as liposomes, virus-like particles, multiple-antigen peptides (MAPs) and the like are also available to a person of skill in the art. Virosomes consist of spherical, unilammelar virus-like particles prepared from a mixture of phospholipids and influenza virus surface glycoproteins, but they do not contain any viral nucleic acids. The hemagglutinin membrane glycoprotein of the influenza virus plays a key role in the mode of action of virosomes. This major antigen of the influenza virus is a membrane fusion-inducing component, which facilitates antigen delivery to immunocompetent cells. Virosomes are known to act as efficient and highly effective means of enhancing the immune response with an excellent safety profile.

The virosome delivery system of the invention further potentiates the immune response against *Candida* infections elicited by the tSap2 polypeptide of the present invention. Virosomes can further be loaded simultaneously with several different B-cell and T-cell epitopes (Poltl-Frank, F. et al., Clin. Exp. Immunol., 1999, 117, 496; Moreno, A. P. et al., J. Immunol., 1993, 151: 489) including universal T-helper cell epitopes (Kumar, A. et al., J. Immunol. 1992, 148, 1499-1505) and other epitopes known to those of skill in the art.

As evidenced by the results shown herein, virosomes have great potential in the design of combined vaccine/adjuvant systems. Furthermore, virosome-based protein vaccines are expected to be safe, since virosome-based protein vaccines have already shown a very good safety profile in humans (Glueck, R., Vaccine 1999, 17, 1782). The concerted action of the tSap2 polypeptide of the present invention, optionally combined with an adjuvant such as CT (cholera toxin) or HLT (a mucosal surface protein derived from E. cob) together with the use of virosomes as an efficient human-compatible delivery system, represents a significant advance in the design of prophylactic as well as therapeutic vaccines against candidiasis, be it vaginal, oesophageal, or systemic.

The present invention also provides for the use of the immunostimulatory compositions, such as the tSap2 polypeptide in combination with a suitable adjuvant and/or virosomes or equivalent delivery vehicles in a suitable pharmaceutical formulation. Accordingly, one or more polypeptides or polypeptide-containing compositions of the invention may be used to prepare a prophylactic or therapeutic vaccine for administration to an individual in need thereof. Such a vaccine which contains one or more of the tSap2 polypeptide-containing compositions of the present invention, as the principal or member active ingredient, can be administered in a wide variety of therapeutic/prophylactic dosage forms in the conventional vehicles for topical, mucosal (nasal, vaginal, oral), systemic, local, and parenteral administration. Thus, the invention provides compositions for parenteral administration which comprise a solution of the tSap2 polypeptide optionally in combination with a suitable adjuvant and/or virosomes or equivalent delivery vehicles dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others. Actual methods for preparing parenterally administrable compounds will be known or apparent to those skilled in the art and are described in more detail in for example, Remington: The Science and Practice of Pharmacy ("Remington's Pharmaceutical Sciences") Gennaro AR ed. 20th edition, 2000: Williams & Wilkins PA, USA, which is incorporated herein by reference.

The route and regimen of administration will vary depending upon the stage or severity of the condition to be treated, and is to be determined by the skilled practitioner. For example, the tSap2 polypeptide and compositions containing it can be used for preparing a pharmaceutical composition that can be administered in subcutaneous, intradermal, or topical or mucosal (vaginal, nasal), or intramuscular form. In preferred embodiments, the pharmaceutical compositions according to the invention can be administered intravaginally. All of these forms are well known to those of ordinary skill in the pharmaceutical arts.

Advantageously, suitable formulations of the present invention may e.g. be administered in a daily dose which may be repeated daily, weekly, or monthly. Furthermore, compounds of the present invention, particularly those containing virosomes or liposomes, can be administered in intravaginal or intranasal form, or via transdermal routes known to those of ordinary skill in the art. To be administered in the form of a transdermal delivery system, the dosage administration will, or course, be continuous rather than intermittent throughout the dosage regimen.

The tSap2 polypeptide and compositions containing it of the present invention may be used to prepare a pharmaceutical composition comprising the active compound in combination with a pharmaceutically acceptable carrier adapted for intravaginal administration. Intravaginal pharmaceutical compositions may be, for example, in the form of a solution, cream, ointment, gel, lotion, foam or aerosol formulation adapted for application to the mucosa. These intravaginal pharmaceutical compositions containing the compounds of the present invention ordinarily include about 0.005% to 5% by weight of the active compound in admixture with a pharmaceutically acceptable vehicle.

The prophylactic or therapeutic compositions of the present invention are for administration in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The preparations of the invention are administered in effective amounts. An effective amount is that amount of a pharmaceutical preparation that alone, or together with further doses, stimulates the desired response. Generally, doses of immunogens ranging from 0.01 µg/kilogram to 500 µg/kilogram body weight, depending upon the mode of administration, are considered effective. The preferred range is believed to be between 0.1 µg/kilogram and 10 µg/kilogram body weight. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be addressed with no more than routine experimentation.

The dosage regimen utilizing the compositions of the present invention is selected in accordance with a variety of factors, including for example species, age, weight, and medical condition of the patient, the stage and severity of the condition to be treated, and the particular compound thereof employed. A physician of ordinary skill can readily determine and prescribe the effective amount of the vaccine required to prevent, counter, or arrest the progress of a malignancy or infectious disease. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, and is within the ability of the skilled practitioner.

In the uses of the present invention, the compounds herein described in detail can form the active ingredient and are typically administered in admixture with suitable pharmaceutical diluents or excipients suitably selected with respect to the intended form of administration, that is, oral tablets, capsules, elixirs, syrups, and the like, and consistent with conventional pharmaceutical practices. For instance, for vaginal administration in the form of a tablet or capsule, the active vaccine component can be combined with a non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

For parenteral administration, sterile suspensions and solutions are desired. Isotonic preparations which generally contain suitable preservatives are employed when intravenous administration is desired. Intravaginal or intraesophageal preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, gels, foams, and lotions, in cream or gel formulations especially suited for mucosal applications.

The tSap2 polypeptide, compositions, or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels. Generally, subjects can receive an intravaginal administration of an effective amount of the tSap2 polypeptide and compositions either in combination with delivery vectors, such as virosomes and/or additional adjuvants, or by themselves. The tSap2 polypeptide of the present invention can also used to prepare a pharmaceutical composition that may be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

Initial doses can be followed by booster doses, following immunization protocols standard in the art. The immunostimulatory effect of the compositions and methods of the instant invention can be further increased by combining any of the above-mentioned tSap2 polypeptide compositions, including their combination with virosomes, with an immune response potentiating compound. Immune response potentiating compounds are classified as either adjuvants or cytokines. Adjuvants may enhance the immunological response by providing a reservoir of antigen (extracellularly or within macrophages), activating macrophages and stimulating specific sets of lymphocytes.

In the case the polypeptide according to the invention is used for preparing a pharmaceutical composition for treating an infectious disease, such as candidiasis, the desired response is control of the infection and/or clearance of the infectious agent from the system. In the case of prophylaxis, the desired response is protective immunity to the agent, as measured by secondary immune responses upon exposure to the agent or an antigen thereof. These desired responses can be monitored by routine methods or can be monitored according to diagnostic methods of the invention discussed herein. The present invention is not to be limited in scope by the specific embodiments described herein. Indeed, various modifications of the invention in addition to those described herein will become apparent to those skilled in the art from the foregoing description, as well as from the examples. Such modifications are intended to fall within the scope of the appended claims.

EXAMPLES

The following examples are provided to better illustrate the claimed invention and are not to be interpreted as limiting the scope of the invention. To the extent that specific materials are mentioned, this is merely for purposes of illustration and is not intended to limit the invention. Unless otherwise specified, biochemical and molecular biology procedures, such as those set forth in Voet, *Biochemistry*, Wiley, 1990; Stryer 1995; *Peptide Chemistry. A Practical Textbook,* 2nd ed., Miklos Bodanszky, Springer-Verlag, Berlin, 1993; Sambrook et al., Molecular Cloning, Cold Spring Harbor Laboratory (2001), Ausubel et al. (Eds.) Current Protocols in Molecular Biology, John Wiley & Sons (2000) are used. One skilled in the art may develop equivalent means or reactants without the exercise of inventive capacity and without departing from the scope of the invention. It will be understood that many variations can be made in the compositions and procedures herein described while still remaining within the bounds of the present invention. Likewise, it is understood that, due to known structural or chemical similarities such as polarity, bulk, or orientation between amino acid side chains, peptide sequences with amino acids or replacement structures equivalent to those disclosed herein will retain similar function. It is the intention of the inventors that such variations are included within the scope of the invention.

Example 1

Materials and Methods 1.1 Microorganisms and Growth Conditions

*C. albicans* ATCC20955 was used as a fungal DNA source in this study. It was grown in Winge (0.3% yeast extract, 0.2% glucose, Difco). *Escherichia coli* M15 ($nal^s$, $str^s$, $rif^s$, $lac^-$, $ara^-$, $gal^-$, $mtl^-$, $F^-$, $recA^+$, $uvr^+$, [pUHA1]) was used as host strains for recombinant plasmids. *E. coli* cells were typically grown in LB-broth (1% tryptone, 0.5% yeast extract, 0.5 NaCl, pH 7.00) or LB-plates (1% tryptone, 0.5% yeast extract, 0.5% NaCl, 1.5% agar, pH 7.00) supplemented when necessary with ampicillin (50 mg $ml^{-1}$), kanamycin (50 mg $ml^{-1}$) (Boehringer). *C. albicans* SA-40 initially isolated from the vaginal secretion of a subject with acute vaginitis was used for experimental vaginitis. The modalities of fungal growth, induction and assessment of experimental vaginal infection in oophorectomized rats were as previously described (Cassone A. et al., Infect. Immun. (1995), 63: 2619-2624; De Bernardis F. et al., Infect. Immun. (1997), 65: 3309-3405).

1.2 Cloning of the SAP2 Coding Sequence

For the molecular cloning of the SAP2 coding sequence, the SAP2 coding sequence was amplified by PCR from the genomic DNA using Ca70 and Ca71 oligonucleotides. A 1% agarose gel was run to verify the correct size of PCR product, and only a single band with an estimated size of approximately 1200 bp was present. Following restriction enzyme digestion, the PCR product was excised from the gel and purified. The coding sequence was ligated into the digested vector to give pRLV141 plasmid. To verify the sequence of the inserts and the frame of the recombinant His-tagged-proteins, pRLV141 and pRLV143 were completely sequenced by Genenco (Italy).

1.3 Expression and Purification of Recombinant *C. Albicans* Proteins

The expression of recombinant 6×his-Sap2 was obtained in *E. coli* M15 carrying the lac repressor-producing pUHA1 plasmid (La Valle R. et al., Infect. Immu. (1995), 63: 4039-4045; Hochuli E. et al., Bio/Technology (1988), 6:1321-1325). Induction was performed in LB medium containing kanamycin and ampicillin, by the addition of isopropyl-b-D-thio-galacto pyranoside (IPTG; Boehringer) with a final concentration of 1 mM, to a culture with an $O.D._{600}$ of 0.7, followed by further 5 h of incubation at 37° C. Recombinant 6×his-tagged protein was purified by nickel-chelate affinity chromatography (Hochuli E. et al., Bio/Technology (1988), 6:1321-1325) according to the manufacturer's instructions (Qiagen; denaturing conditions). Fractions containing the purified polypeptide were pooled and precipitated with 3 volumes of absolute ethanol, resuspended in water and stored at −20° C. In the induced cells, a new protein band with a molecular size of about 48 kDa, consistent with the predicted size of 6×his-SAP2, was observed.

Example 2

2.1 Construction of Recombinant Plasmids and Production of Truncated Recombinant Sap2 (tSap2)

Full-length SAP was cloned as described in Example 1. For the production of a truncated form of Sap2, plasmid pRLV141 was digested with BamHI to excise the fragment corresponding to the nucleotides encoding amino acids 1-76 of SAP2 coding sequence. The digested plasmid was re-ligated to give pRLV143 and used to transform the bacterial cells. The resulting colonies were analyzed for DNA insert length by restriction mapping, PCR and DNA sequencing (data not shown).

Alternatively a truncated Sap2 including the His-tag and with an additional protease cleavage site (thrombin) between the His-tag and tSap2 was produced synthetically (Geneart, Regensburg, Germany). For optimal expression in a host system the codon usage was adapted to the host's codon usage (e.g. by Geneart, Regensburg, Germany). The tSap2 gene was synthesized with the two restriction sites NdeI (5' end) and BamHI (3' end) and cloned into the NdeI/BamHI restriction sites of the expression vector pET-14b (Novagen/Merck Biosciences, Darmstadt, Germany), resulting in the plasmid pET14-tSap2. The tSap2 nucleotide sequence in this vector was confirmed by sequencing.

Alternatively a truncated Sap2 which lacks the His-tag was produced synthetically (Geneart, Regensburg, Germany). For optimal expression in a host system the codon usage was adapted to that of the host (Geneart, Regensburg, Germany). The tSap2 gene was synthesized with the two restriction sites NcoI (5' end) and BamHI (3' end) and cloned into the NcoI/BamHI restriction sites of the expression vector pET-14b (Novagen/Merck Biosciences, Darmstadt, Germany), resulting in the plasmid pET-tSap2. The tSap2 nucleotide sequence in this vector was confirmed by sequencing.

2.2 Expression and Purification of Recombinant *C. albicans* Proteins

The expression of recombinant 6×his-tSAP2 (6×his-SAP2[77-398]) polypeptide was obtained in *E. coli* M15 carrying the lac repressor-producing pUHA1 plasmid (La Valle R. et al., Infect. Immu. (1995), 63: 4039-4045; Hochuli E. et al., Bio/Technology (1988), 6:1321-1325). Induction was performed in LB medium containing kanamycin and ampicillin, by the addition of isopropyl-b-D-thio-galacto pyranoside (IPTG; Boehringer) with a final concentration of 1 mM, to a culture with an $O.D._{600}$ of 0.7, followed by further 5 h of incubation at 37° C. Recombinant 6×his-tagged protein was purified by nickel-chelate affinity chromatography (Hochuli E. et al., Bio/Technology (1988), 6:1321-1325) according to the manufacturers instructions (Qiagen; denaturing conditions). Fractions containing the purified polypeptide were pooled and precipitated with 3 volumes of absolute ethanol, resuspended in water and stored at −20° C. In the induced cells, a new protein band with a molecular size of about 35.5 kDa consistent with the predicted size of 6×his-tSAP2 was observed.

The expression of pET14-tSap2 and pET-tSap2 was performed in expression host systems which are lysogens of bacteriophage λDE3, e.g. *E. coli* BL21(DE3) or *E. coli* Origami(DE3) (Novagen/Merck Biosciences, Darmstadt, Germany), under conditions as described above.

Proteolytic removal of the His-tag and isolation/purification of the resulting recombinant tSAP2 protein without His-tag was performed as follows: 6×his-tagged protein with a thrombin. cleavage site (from vector pET14-tSap2) was purified by nickel-chelate affinity chromatography on a HITRAP FF Crude column according to the manufacturer's instructions (GE Healthcare, Dübendorf, Switzerland).

The pool of the purified protein was treated with the protease thrombin to remove the 6×his tag from the tSap2 protein. Therefore, the purified protein pool was incubated with thrombin-agarose beads for 5 h at RT as recommended by the manufacturer (Sigma, Buchs, Switzerland). The untagged tSap2 protein was loaded on an ion exchange chromatography column (HITRAP Q FF, GE Healthcare, Dübendorf, Switzerland) and eluted with buffer B (1×PBS, pH 7.4; 1.5 M NaCl) with a gradient to 100% buffer B over 5 column volumes (CV). The fractions containing tSap2 were pooled and dialysed against 1×PBS, pH 7.4.

Isolation/purification of recombinant tSAP2 protein without His-tag was performed as follows:

The expression of the pET-tSap2 vector in *E.coli* was performed as described above for pET14-tSap2. After cultivation, the cells were centrifuged to a pellet and treated with BUGBUSTER reagent as indicated by the manufacturer (Novagen/Merck Biosciences, Darmstadt, Germany) to isolate the inclusion bodies (IB). Finally, the IB were resuspended in 20 mL of lysis buffer per liter of bacteria culture (lysis buffer: 1×PBS, pH 7.4; 4 M urea). This material was loaded onto a HITRAP Q FF column (GE Healthcare, Dübendorf, Switzerland) and eluted with buffer B (1×PBS, pH 7.4; 4 M urea, 1 M NaCl) with a gradient to 100% buffer B over 5 column volumes (CV). The fractions containing tSap2 were pooled and dialyzed to 1×PBS, pH 7.4, 0.25 M urea in several steps (4 M urea →2 M urea →1 M urea →0.5 M urea →0.25 M urea), each time for 24 h at 4° C., 1 L volume. Afterward, this material was loaded on a HITRAP Q FF column (GE Healthcare, Dübendorf, Switzerland), with buffer A (1×PBS, pH 7.4, 10 mM NaCl) and buffer B (1×PBS, pH 7.4, 1.5 M NaCl), and a gradient to 100% buffer B over 5 CV. The fractions containing tSap2 were pooled and concentrated on a Amicon Ultra 10K column (Millipore, Zug, Switzerland) according to the instructions. The buffer was changed to 1×PBS, pH 7.4, 1.5 M NaCl by the addition of NaCl. This material was loaded onto a HITRAP Phenyl FF column (GE Healthcare, Dübendorf, Switzerland), with buffer A (1×PBS, pH 7.4, 1.5 M NaCl) and buffer B (1x PBS, pH 7.4,10 mM NaCl), and a gradient to 100% buffer B over 10 CV. The fractions containing tSap2 were pooled and concentrated on a Amicon Ultra 10K column (Millipore, Zug, Switzerland) and washed three times with 1×PBS, pH 7.4, 10 mM NaCl. The protein was stored in aliquots at 4° C. and frozen.

Example 3

Stability of Recombinant Sap and tSap2

Recombinant Sap2 and tSap2 were expressed and purified as described in Example 1 and 2. 3 µg of recombinant Sap2 and tSap2 were incubated in PBS for different lengths of time (30 min to 24 or 48 hours) either at room temperature or at 37° C. After incubation, both preparations were subjected to SDS-PAGE and stained with COOMASSIE BLUE.

The truncated recombinant Sap2 was fully stable and fully reactive with the anti-Sap2 serum for 24 hours (FIG. 1A) and 48 hours (data not shown), without any sign of degradation. Following incubation at RT (at 37° C.), this protein preparation was also very stable and showed only little degradation with serum-reactive low-molecular weight bands at 24-48 hours. In contrast, the wild type Sap2 preparation was labile following incubation for 6 to 24 hours even at room temperature and totally degradable even after short, 30 min incubation at 37° C. (FIG. 1B).

Example 4

Standard Methods as Used in the Following Experiments 4.1 Immunogenicity of Recombinant Sap2 and tSap2
4.1.1 Animals Oophorectomized female Wistar rats (80-100 g) from Charles River Breeding Laboratories (Calco, Italy) were used throughout this study. Animal maintenance and overall care were as described elsewhere (De Bernardis F. et al., Infect. Immun. (1997), 65: 3309-3405).
4.1.2 Intravaginal Immunization in Rats For active immunization, groups of five rats were administered, a total of three times, by intravaginal (i.v.g.) route at weekly intervals with 1-100 µg of recombinant SAP2 and tSAP2 preparation and optionally together with adjuvants (e.g. HLT ug). Control animals received only sterile saline.
4.1.3 Vaginal Wash The rat vaginal cavity was washed by gentle injection and subsequent aspiration of 0.5 ml PBS. The collected fluids were pooled for each experimental group; the resultant 2.5 ml were centrifuged for 15 minutes at 3500×g in a refrigerated Biofuge, and the supernatant was assayed for vaginal antibodies.
4.2 ELISA to Detect Abs Against *C. albicans* Constituents in Vaginal Fluids The presence of antibodies was assayed in the vaginal washes by a previously described enzyme-linked immunoadsorbent assay (ELISA) (Cassone A. et al., Infect. Immun. (1995), 63: 2619-2624; De Bernardis F. et al., Infect Immun. (2000), 68: 3297-15 3304). 200 µl of a purified native Sap2 preparation (kindly provided by P.A. Sullivan, Massey, University, Palmerston North, New Zealand) (5 µg/ml in 0.2 M sodium carbonate) was used as coating antigen for the detection of antibodies and was dispensed into the wells of a polystyrene micro titration plate, which was kept overnight at 4° C. After three washes with TWEEN 20-PBS buffer, 1:2 dilutions of vaginal fluids were distributed in triplicate wells and the plates were incubated for 1 h at room temperature. Each well was washed again with TWEEN 20 PBS buffer and predetermined optimal dilutions of alkaline phosphatase-conjugate, sheep anti-rat immunoglobulin IgG or IgA (obtained from Serotec Ldt; Kidlington, Oxford, United Kingdom) were added. Bound alkaline phosphatase was detected by the addition of a solution of para-nitrophenyl phosphate in diethanolamine buffer and the plates were read at A 405 with an automated micro reader (Labsystem Multiscan, MS, Finland) blanked against air. Vaginal fluid was considered positive for a determined antibody when the O.D. was greater than 2 times the value of the well coated with the same antigen and tested with the vaginal fluid of non-immunized, uninfected rats.

Quantitative variables were tested for normal distribution and compared by means of Student's two tailed t-test. Differences in group proportions were assessed by use of the $x^2$ test or, for small numbers with the Fisher's exact test. ANOVA analysis of variance was used for comparing paired samples. Two-tailed test of significance at the p<0.05 level were used to determine statistical significance. All statistical analysis was performed using the software program Intercooled Stata (Stata Corporation, Texas).

Example 5

Detection of tSAP2 Antibodies in Immunised Rats

Figure 2:
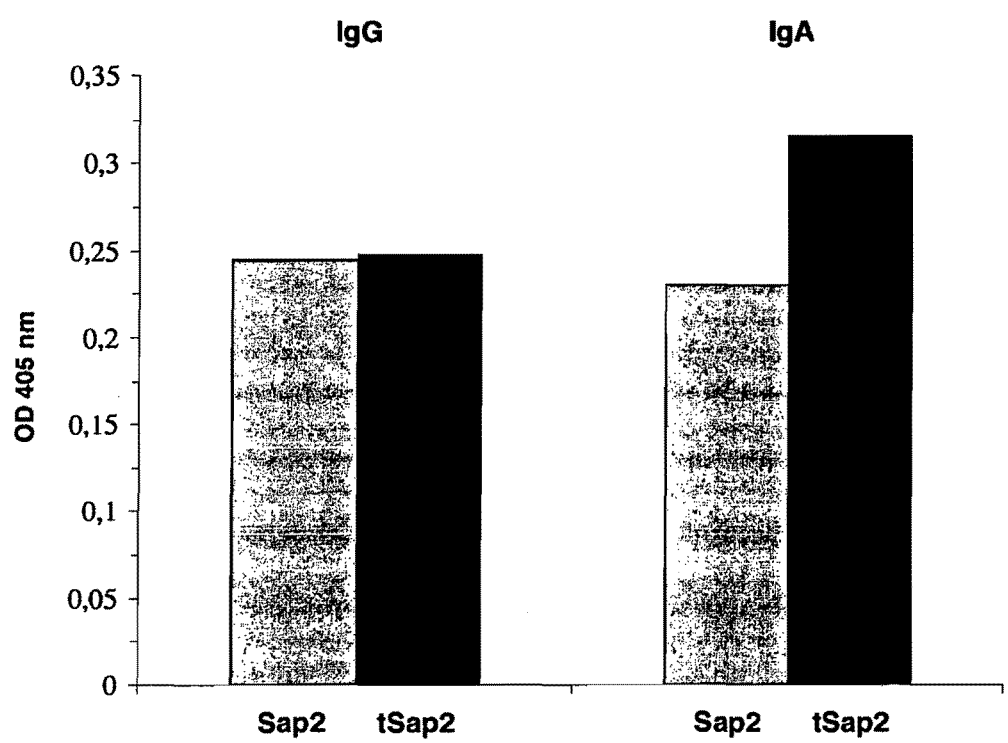
FIG. 2 demonstrates that the truncated Sap2 (tSap2) induces higher antibody levels than the enzymatically active wild type Sap2 (Sap2) in vaginal fluids of immunized rats. The increase in antibody production is observed mostly for IgA, the main immunoglobulin involved in the mucosal immunity. The antibody levels were measured in pools of vaginal fluids from rats immunized with wild type Sap2 preparation and rats immunized with truncated, recombinant Sap2 (tSap2) by ELISA. The presence of antibody in the vaginal fluids is expressed in terms of absorbance, which was read at $\lambda=405$ nm.

Two groups of five female ovarectomized rats were immunized by intravaginal route three times at weekly intervals: one group received 100 μg/dose of wild type Sap2 whereas the second group was administrated 20 μg/dose of truncated Sap2. One week after the last immunization, pools of vaginal washes were collected from each group and then were diluted 1:2 for the ELISA (standard methods outlined in Example 4) A wild type Sap2 preparation was used as coating antigen for the antibody detection in the immunological assay. The presence of antibody specific for the wild type Sap2 in the vaginal fluids is expressed in terms of absorbance, which was read at $\lambda=405$ nm. The increase in antibody production is observed mostly for IgA, the main immunoglobulin involved in the mucosal immunity. The results are shown in FIG. 2 and demonstrate that the truncated Sap2 (tSap2) induces higher antibody levels than the enzymatically active wild type Sap2 (Sap2) in vaginal fluids of immunized rats.

Example 6

Protection of *C. albicans* Challenge after Vaccination with Sap2 and tSap2

Figure 3:
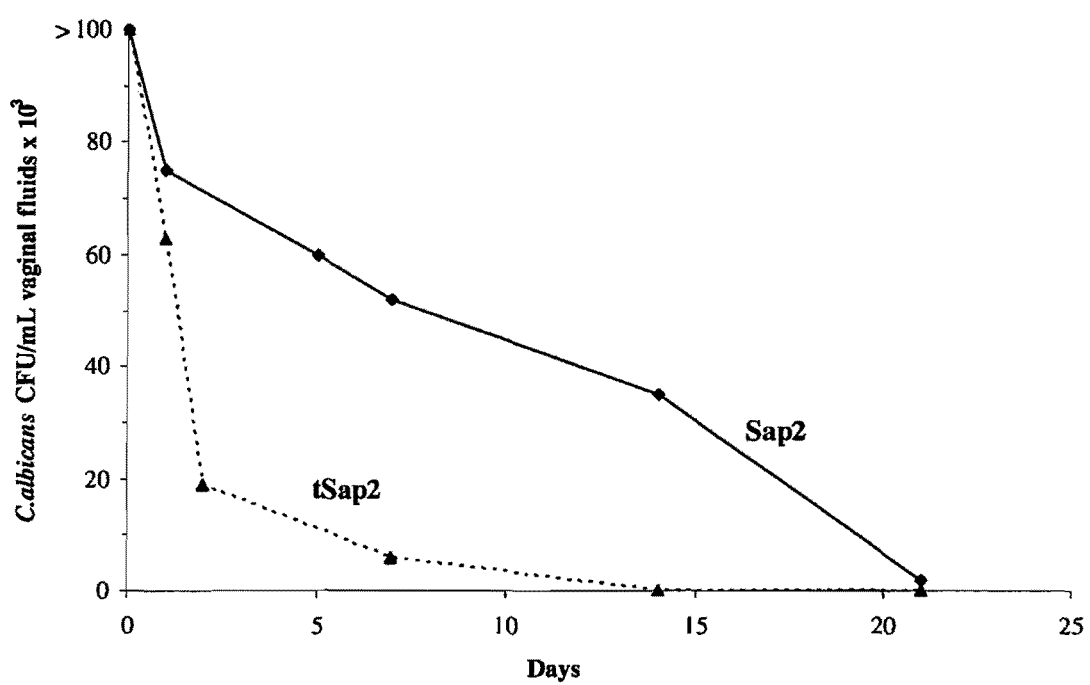
FIG. 3 shows that the immunization of rats with the truncated protein (tSap2) resolves the vaginal infection by *C. albicans* faster than the treatment with the wild type protein (Sap2) in an animal challenge model. Two groups of five female ovarectomized rats were immunized by intravaginal route three times at weekly intervals: one group received 100 μg/dose of wild type Sap2 (-■-), whereas the second group received 50 μg/dose of truncated Sap2 (-▲-). One week after the last immunization all rats were challenged with a vaginopathic dose of the *C. albicans* strain SA-40. The clearance of the fungal cells from the treated rats was evaluated by counting the *C. albicans* colony forming units (CFU) in the vagina for 21 days after the challenge. In particular, the yeast cells were counted by culturing 1 μl samples of vaginal fluid on Sabouraud agar containing chloramphenicol, at 28° C. for 72 hours.

One week after the last immunization, all animals were challenged i.v.g. with $10^7$ cells of *C. albicans*, and the infection monitored by enumeration of colony forming units (CFU), as reported elsewhere (De Bernardis F. et al., Infect. Immun. (1997), 65: 3309-3405; De Bernardis F. et al., Infect. Immun. (2000), 68: 3297-3304). Two independent experiments were carried out. For antibody (Ab) analysis, samples of vaginal fluids were taken at regular intervals from each animal by gently washing the vaginal cavity with 0.5 ml of PBS, as described elsewhere (De Bernardis F. et al., Infect. Immun. (1997), 65: 3309-3405; De Bernardis F. et al., Infect. Immun. (2000), 68: 3297-3304). The collected fluid was centrifuged at 3500×g for 15 min in a refrigerated Biofuge, and the supernatant was assayed as described above. The results are shown in FIG. 3.

Example 7

Virosome-based Formulations Containing tSap2 Induce Higher IgG and IgA Levels

Figure 4:
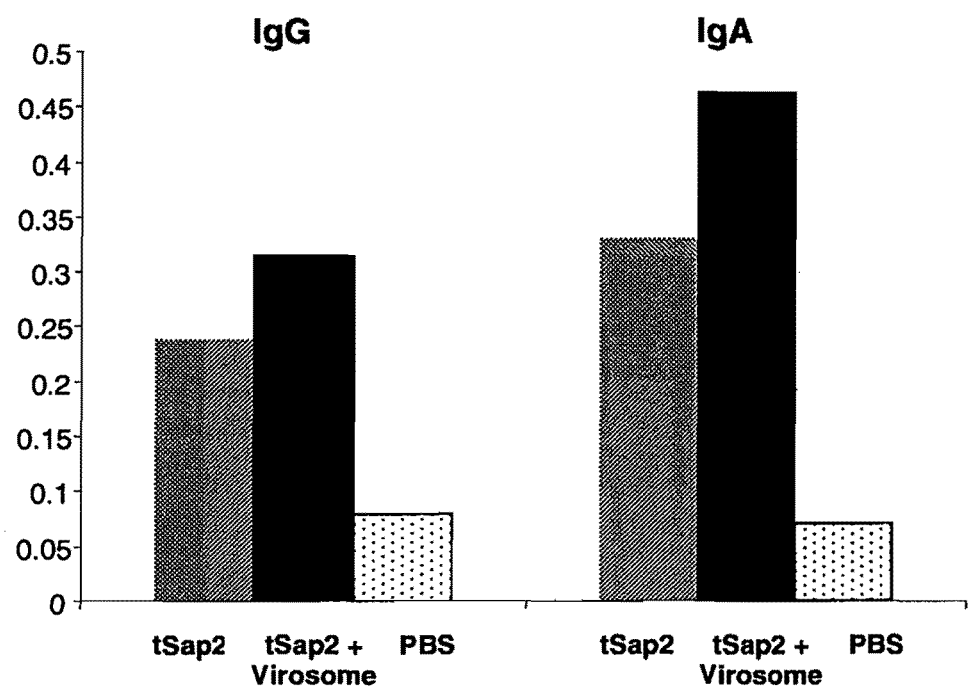
FIG. 4 shows that the virosome-based formulations containing the truncated Sap2 protein induce higher anti-Sap2 IgG and IgA levels than the truncated protein alone in the vagina of immunized rats. The antibody levels were evaluated by ELISA performed on pools of vaginal fluids from rats treated with different preparations. The presence of antibody in the vaginal fluids is expressed in terms of absorbance, which was read at $\lambda=405$ nm.

Three groups of five rats were immunized intravaginally three times at weekly intervals: the first group received 20 μg/dose of truncated protein alone; the second group received 20 μg/dose of truncated protein linked to the virosome surface, and the third group was treated with buffer. One week after the last immunization pools of vaginal washes were collected from each group and were 1:2 diluted for the ELISA. A wild type Sap2 preparation was used as coating antigen for the antibody detection in the immunological assay. The presence of antibody in the vaginal fluids is expressed in terms of absorbance, which was read at $\lambda=405$ nm. The results are shown in FIG. 4.

Example 8

Figure 5:
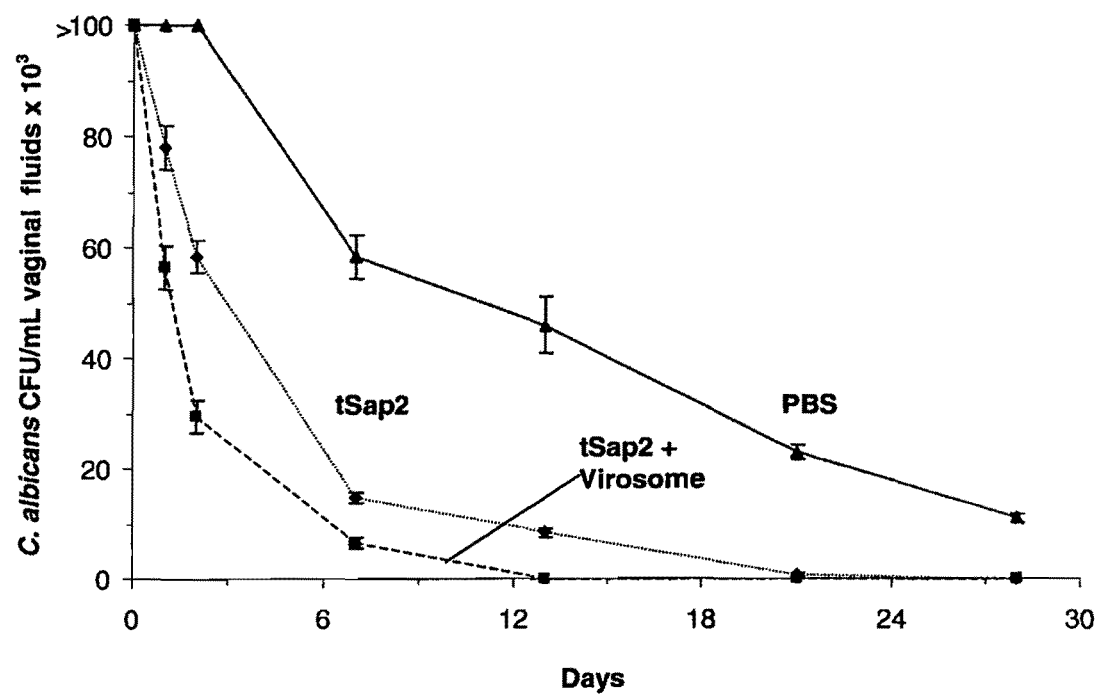
FIG. 5 demonstrates that the truncated protein bound to virosomes endows a higher rate of infection clearance if compared with the truncated protein alone, in the vagina of infected rats. The clearance rate was measured by monitoring the status of vaginal infection in immunized and challenged rats over time. Colony forming units (CFU) were counted 1, 2, 7, 13, 21 and 28 days after the challenge.

Virosome-based Formulations Containing tSap2 Endow a Higher Rate of Infection Clearance Specifically, three groups of 5 female ovarectomized rats were immunized with different preparations following the usual immunization scheme: the first group received 20 μg/dose of truncated protein alone, the second group received 20 μg/dose of truncated protein linked to the virosome surface, and the third group was treated with buffer. Four weeks after the last immunization all rats were challenged with a vaginopathic dose of the *C. albicans* strain SA-40 and the *Candida* colony forming units (CFU) were counted 1, 2, 7, 13, 21 and 28 days after the challenge. The results are shown in FIG. 5.

Figure 6:
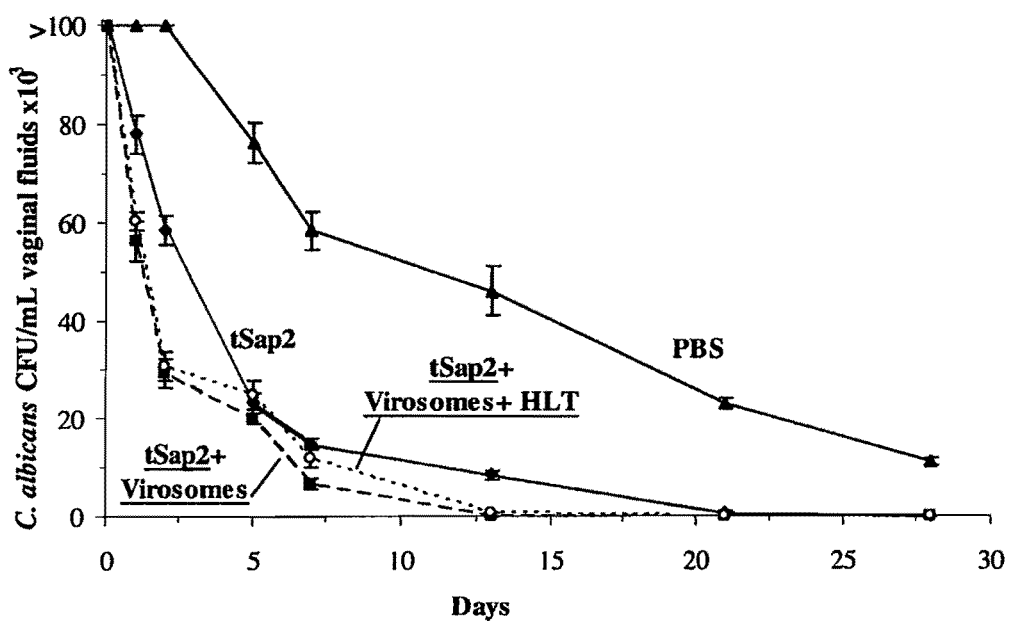
FIG. 6 shows that the truncated protein associated to the virosomes endows a higher rate of infection clearance than the protein alone. The addition of the mucosal adjuvant HLT (heat labile toxin from *E. coli*) to the virosome-based formulation does not confer any advantage in terms of protection. The course of the vaginal infection was monitored for 28 days.

Four groups of female ovarectomized rats were immunized intravaginally three times, at weekly intervals with the following preparations: 1) truncated protein Sap2 linked to virosomes (20 μg/dose); 2) truncated protein Sap2 linked to virosomes and combined with HLT (20 μg/dose); 3) truncated protein alone (20 μg/dose); 4) buffer. One month after the last treatment all rats were challenged with a vaginopathic amount of *C. albicans*. The course of the vaginal infection was monitored for 28 days. The results are shown in FIG. 6.

Example 9

Virosomes Containing the tSap2 Protein Confer a Better Protection

In this in vivo experiment, two groups of female ovarectomized rats were immunized intravaginally three times, at weekly intervals with virosomes containing the truncated protein and the truncated protein alone, respectively. Four weeks after the last immunization all rats were challenged with a vaginopathic dose of the *C. albicans* strain SA-40. The status of vaginal infection was monitored for 28 days by enumeration of colony forming units (CFU). A rat was considered infected when CFU≥1×10³/ml vaginal fluid. The results are shown in Table 1.

TABLE 1

| | Day = 0 | | Day = 7 | |
|---|---|---|---|---|
| Formulations | CFU/mL vaginal Fluids ×10³ | Infected rats | CFU/mL vaginal Fluids ×10³ | Infected rats |
| tSap2 + IRIV | >100 | 5/5 | 4 ± 3 | 2/5 |
| tSap2 | >100 | 5/5 | 6 ± 2 | 3/5 |
| PBS | >100 | 5/5 | >100 | 5/5 |

Table 1: The table shows that the virosomes containing the truncated protein confer a better protection in an animal challenge model than the protein alone. Specifically, the number of infected rats immunized with the virosome-based formulation is lower than the number of rats treated with the protein alone, one week after the challenge.

Example 10

Coupling Sap2/tSap2 to Phosphoethanolamine 10.1 Coupling of *Candida* Protein to Phosphoethanolamine Via Cysteine Groups For a virosomal preparation of 4 ml, the designated amount of the protein is taken and resuspended in 1 ml of 100 mM OEG in PBS. This solution is transferred to 50 mg immobilized Tris-(2-carboxyethyl) phosphine (TCEP) on Amberlite Beads (Merck Biosciences Novabiochem, Läufelfingen, Switzerland) and incubated for 30 min at RT. The beads are removed and the solution is transferred to 4 mg of fresh N-MCC-PE (ca. 4.3 µmol; Avanti Polar Lipids, Alabaster, Ala.) and incubated at 30° C. under shaking for at least 4 h. Finally, unused maleimide groups in the phosphoethanolamine are consumed by the addition of trace amounts of Tris buffer pH 7.4. The solution is stored at 4° C. until use.

10.2 Coupling of *Candida* Protein to Phosphoethanolamine Via Primary Amino Groups For a virosomal preparation of 4 ml, the designated amount of the protein is taken and resuspended in 0.1-0.5 ml of PBS pH 7.4, 10 mM EDTA. This solution is added to 12.5 mg Sulfo-SMCC reagent (approx. 25 µmol; Apollo Scientific, Cheshire, United Kingdom) and incubated for 1 h at RT under slow shaking. Unused Sulfo-SMCC reagent is removed by gel filtration over a SEPHADEX column (GE Healthcare, Otelfingen, Switzerland) and complemented with 100 mM OEG in PBS to a final volume of 1 ml. This mixture is then added to 4 mg of fresh N-MCC-PE (ca. 4.3 µmol; Avanti Polar Lipids, Alabaster, Alabama) and incubated at RT under shaking for at least 4 h. Finally, unused maleimide groups in the phosphoethanolamine are consumed by the addition of trace amounts of Tris buffer pH 7.4. The solution is stored at 4° C. until use.

Example 11

Vaccine Containing Sap2 or tSap2 in Combination with Virosomes 11.1 Reagents Used in Preparation and Working Examples Reagents: Octaethyleneglycol-mono-(n-dodecyl)ether (OEG, $C_{12}E_8$), was purchased from Fluka Chemie GmbH-(Buchs, Switzerland). Sucrose (Eur. Phar.) was purchased from Merck (Dietikon, Switzerland). Egg phosphatidyl choline (PC) was obtained from Lipoid (Cham, Switzerland). 1-Oleoyl-3-palmitoyl-rac-glycero-2-phosphoethanolamine was obtained from Bachem (Bubendorf, Switzerland). Bio-Beads SM2 were purchased from Bio-Rad Laboratories (Glattbrugg, Switzerland). Cholesteryl N-(trimethylammonioethyl)carbamate chloride (TC-chol) was purchased from Merck Eprova (Schaffhausen, Switzerland).

Influenza viruses of the A/Singapore/6/86 (AlSing) strain and other influenza A strains, propagated in the allantoic cavity of embryonated eggs (Gerhard, W. (1976), J. Exp. Med. 144: 985-995), were obtained from Berna Biotech AG (Bern, Switzerland) and purified as described (Skehel, J. et al., (1971), Virology 44: 396). The hemagglutinin/phospholipid ratio was determined according to Bottcher (Bottcher et al. (1961). Anal. Chim. Acta 24, 203), and HA-quantification after SDS-PAGE was conducted using the COOMASSIE BLUE-extraction method as described by Ball (Ball (1986), Anal. Biochem. 155, 23).

11.2 Preparation of the Virosomes

For the preparation of PE-mimetic-IRIV, a solution of purified Influenza A/Singapore hemagglutinine (4 mg) in phosphate buffered saline (PBS) was centrifuged for 30 min at 100 000 g and the pellet was dissolved in PBS (1.33 ml) containing 100 mM octaethyleneglycolmonodecylether (PBS-OEG). Amyloid-peptide-phosphatidylethanol-amine conjugates (4 mg), phosphatidylcholine (32 mg; Lipoid, Ludwigshafen, Germany) and phosphatidyl-ethanolamine (6 mg) were dissolved in a total volume of 2.66 ml of PBS-OEG. The phospholipids and the hemagglutinine solutions were mixed and sonicated for 1 min. This solution was centrifuged for 1 hour at 100 000 g and the supernatant was sterilized by filtration. Virosomes were formed by detergent removal (SM BioBeads, BioRad, Glattbrugg, Switzerland).

11.3 Preparation of SAP2/tSAP2 Coupled to Virosomes (Protein-GIRIVs)

Protein-GIRIVs are prepared by the detergent removal method. For a final volume of 4 ml, 32 mg egg PC and 4 mg PE are dissolved in 2 ml of PBS, 100 mM OEG (PBS/OEG) and the prepared protein-PE conjugate (1 ml; see above) is added to this mixture. 2 mg HA of inactivated influenza A/Singapore/6/86 virus is centrifuged at 100,000×g for 1 h at 4° C. and the pellet is dissolved in 1 ml of PBS/OEG. The detergent solubilised phospholipids and viruses are mixed and sonicated for 1 min. This mixture is centrifuged at 100,000×g for 1 h at 18° C. and the supernatant is taken for further steps. Virosomes are then formed by detergent removal using two times 1.5 g of wet SM2 Bio-Beads for 1 h each at room temperature with shaking. The virosome solution is stored at 4° C.

Example 12

Vaccine Containing Sap2 or tSap2 in Combination with Lyophilized Virosomes 12.1 Preparation of Virosomes Containing TC-Chol Virosomes containing TC-Chol are prepared by the detergent removal method. For a final volume of 4 ml, 32 mg egg PC, 8 mg OPPE and 5 mg cholesteryl N-(trimethylammonioethyl)carbamate chloride (TC-chol) are dissolved in 2.6 ml of PBS, 100 mM OEG (PBS/OEG). 2 mg HA of inactivated A/Singapore/6/86 influenza virus or another influenza A strain is centrifuged at 100,000×g for 1 h at 4° C. and the pellet is dissolved in 1 ml of PBS/OEG. The detergent solubilised phospholipids and viruses are mixed with 0.4 mL of 50% (w/v) sucrose and sonicated for 1 min. This mixture is centrifuged at 100,000×g for 1 h at 18° C. Virosomes are formed by detergent removal using two times 1.5 g of wet SM2 Bio-Beads for 1 h each at room temperature with shaking. The freshly formed virosomes are then sterile filtered (0.22 µm) and aliquoted in sterile glass vials. The closed vials are frozen at −70° C. and then lyophilized at −40° C. for 20 h and 10° C. for 2 h. The closed vials are stored at frozen until use.

12.2 Preparation of SAP2/tSAP2 Coupled to Lyophilizable Virosomes (Protein-TIRIVs)

To obtain TIRIVs with *Candida* protein coupled to a phospholipid ancher, the protein is coupled to PE as described above and dissolved in the solution containing egg PC, PE and TC-Chol in PBS/OEG, before combining with the detergent solubilised viral HA of inactivated H1N1 influenza virus. The detergent solubilised phospholipids and viruses are mixed with sucrose to a final concentration of 5% (w/v) and sonicated for 1 min. This mixture is centrifuged at 100,000×g for 1 h at 18° C. Virosomes with the *Candida* protein coupled to their membrane are then formed by detergent removal using two times 1.5 g of wet Bio-Beads SM2 for 1 h each at room temperature with shaking. The virosomes are sterile filtered (0.22 µm) and aliquoted in sterile glass vials. The closed vials are frozen at −70° C. and then lyophilized at −40° C. for 20 h and 10° C. for 2 h. The closed vials are stored at frozen until use.

Reconstitution of the lyophilized TIRIVs is done with an equal volume of sterile water. The vial is mixed shortly for about 10 sec on the vortex on intermediate level and stored at 4° C. until use.

Example 13

MAbs Against tSAP2 Polypeptide Provide Passive Protection

Groups of five rats were inoculated intravaginally with anti-tSAP2 antibodies that were eluted from immune vaginal fluids by absorption with tSAP2-coated Dynabeads, 30 minutes before administration of a challenge dose of $10^7$ C. albicans cells (strain SA40). The monoclonal anti-tSAP2 antibodies (MAbs) were used at the concentration of 100 μg/ml. The MAbs used throughout this study were MAb NL2/2A8, MAb NL2/9B9 which are directed against the truncated Sap2 protein, and MAb NL2/7C9 which is directed against the enolase recombinant protein.

Quantitative variables were tested for normal distribution and compared by means of the Student's two tailed t-test. Differences in group proportions were assessed by use of the $x^2$ test or, for small numbers, with the Fisher's exact test. The ANOVA analysis of variance was used for comparing paired samples. Two-tailed tests of significance at the $p<0.05$ level were used to determine the statistical significance. All statistical analyses were performed using the software program Intercooled Stata.

As shown in FIG. 7, both anti-tSap2 mAbs (NL2/2A8 and NL2/9B9) conferred protection to rats, by inducing a very rapid clearance of fungal cells from the vagina compared to the controls, namely, rats receiving only C. albicans cells or an anti-enolase mAb. Under the conditions tested, the effect of anti-tSap2 mAbs was substantially comparable to that obtained with fluconazole, a popular antifungal drug, or with pepstatin, a well-known Sap inhibitor, treatment.

The invention claimed is:

1. An isolated polypeptide consisting of the amino acid sequence of SEQ ID NO:1.

2. A composition comprising the isolate polypeptide of claim 1.

3. A vaccine composition against *Candida albicans* comprising:
an isolated polypeptide consisting of the amino acid sequence of SEQ ID NO: 1.

4. The vaccine composition of claim 3, further comprising one or more additional components selected from the group consisting of excipients, diluents, adjuvants, and delivery vehicles.

5. A method of eliciting an immune response against *Candida albicans* in a mammal, wherein the method comprises administering to the mammal a composition comprising the isolated polypeptide of claim 1.

6. The method of claim 5, wherein the composition further comprises one or more additional components selected from the group consisting of excipients, diluents, adjuvants, and delivery vehicles.

7. The method of claim 6, wherein the delivery vehicle is a virosome.

8. The method of claim 7, wherein the isolated polypeptide is linked to the surface of the virosome.

9. The method of claim 7, wherein the isolated polypeptide is contained in the lumen of the virosome.

10. The method claim 9, wherein the isolated polypeptide is both linked to the surface of and contained in the lumen of the virosome.

11. A kit comprising
an isolated polypeptide consisting of the amino acid sequence of SEQ ID NO: 1.

* * * * *

SEQUENCE LISTING

```
<160> NUMBER OF SEQ ID NOS: 10

<210> SEQ ID NO 1
<211> LENGTH: 322
<212> TYPE: PRT
<213> ORGANISM: Candida albicans

<400> SEQUENCE: 1

Gly Ser Asn Asn Gln Lys Leu Asn Val Ile Val Asp Thr Gly Ser Ser
1               5                   10                  15

Asp Leu Trp Val Pro Asp Val Asn Val Asp Cys Gln Val Thr Tyr Ser
            20                  25                  30

Asp Gln Thr Ala Asp Phe Cys Lys Gln Lys Gly Thr Tyr Asp Pro Ser
        35                  40                  45

Gly Ser Ser Ala Ser Gln Asp Leu Asn Thr Pro Phe Lys Ile Gly Tyr
    50                  55                  60

Gly Asp Gly Ser Ser Ser Gln Gly Thr Leu Tyr Lys Asp Thr Val Gly
65                  70                  75                  80

Phe Gly Gly Val Ser Ile Lys Asn Gln Val Leu Ala Asp Val Asp Ser
            85                  90                  95

Thr Ser Ile Asp Gln Gly Ile Leu Gly Val Gly Tyr Lys Thr Asn Glu
        100                 105                 110

Ala Gly Gly Ser Tyr Asp Asn Val Pro Val Thr Leu Lys Lys Gln Gly
    115                 120                 125

Val Ile Ala Lys Asn Ala Tyr Ser Leu Tyr Leu Asn Ser Pro Asp Ala
130                 135                 140

Ala Thr Gly Gln Ile Ile Phe Gly Gly Val Asp Asn Ala Lys Tyr Ser
145                 150                 155                 160

Gly Ser Leu Ile Ala Leu Pro Val Thr Ser Asp Arg Glu Leu Arg Ile
            165                 170                 175

Ser Leu Gly Ser Val Glu Val Ser Gly Lys Thr Ile Asn Thr Asp Asn
        180                 185                 190

Val Asp Val Leu Leu Asp Ser Gly Thr Thr Ile Thr Tyr Leu Gln Gln
    195                 200                 205

Asp Leu Ala Asp Gln Ile Ile Lys Ala Phe Asn Gly Lys Leu Thr Gln
    210                 215                 220

Asp Ser Asn Gly Asn Ser Phe Tyr Glu Val Asp Cys Asn Leu Ser Gly
225                 230                 235                 240

Asp Val Val Phe Asn Phe Ser Lys Asn Ala Lys Ile Ser Val Pro Ala
            245                 250                 255
```

```
Ser Glu Phe Ala Ala Ser Leu Gln Gly Asp Asp Gly Gln Pro Tyr Asp
            260                 265                 270

Lys Cys Gln Leu Leu Phe Asp Val Asn Asp Ala Asn Ile Leu Gly Asp
        275                 280                 285

Asn Phe Leu Arg Ser Ala Tyr Ile Val Tyr Asp Leu Asp Asp Asn Glu
    290                 295                 300

Ile Ser Leu Ala Gln Val Lys Tyr Thr Ser Ala Ser Ser Ile Ser Ala
305                 310                 315                 320

Leu Thr

<210> SEQ ID NO 2
<211> LENGTH: 966
<212> TYPE: DNA
<213> ORGANISM: Candida albicans

<400> SEQUENCE: 2
ggatccaata atcaaaaact taatgttatt gttgatactg gatcatctga tttatgggtt      60
cctgatgtta atgttgattg tcaagtcact tatagtgatc aaactgcaga tttctgtaaa    120
caaaagggga catatgatcc aagtggttca tcagcttcac aagatttgaa tactccattc    180
aaaattggtt atggtgatgg atcttcatct caaggtactt tatataagga taccgttgga    240
tttggtggtg tttcgattaa aaatcaagtt ttagctgatg ttgattctac ttcaattgat    300
caaggtattt taggagttgg ttataaaacc aatgaagccg gtggtagtta tgataatgtc    360
cctgtcactt taaaaaaaca aggagtcatt gctaagaatg cttattcact ttatcttaat    420
tctccagatg ctgccacggg acaaataatt ttcggtgggg ttgataatgc taaatatagt    480
ggttcattaa ttgcattacc agttacttct gatcgtgaat taagaattag tttgggttca    540
gttgaagttt ctggtaaaac catcaatact gataatgtcg atgttctttt ggattcaggt    600
accaccatta cttatttgca acaagatctt gctgatcaaa tcattaaagc tttcaatggt    660
aaattaactc aagattccaa tggtaattca ttctatgaag ttgattgtaa tttgtcaggg    720
gatgttgtat tcaattttag taaaaatgct aaaatttccg ttccagcttc cgaatttgct    780
gcttctttac aaggtgatga tggtcaacca tatgataaat gtcaattact tttcgatgtt    840
aatgatgcta acattcttgg tgataacttt ttgagatcag cttatattgt ttatgatttg    900
gatgataatg aaatttcttt ggctcaagtc aaatatactt ctgcttccag tatttctgcc    960
ttgacc                                                              966

<210> SEQ ID NO 3
<211> LENGTH: 398
<212> TYPE: PRT
<213> ORGANISM: Candida albicans

<400> SEQUENCE: 3

Met Phe Leu Lys Asn Ile Phe Ile Ala Leu Ala Ile Ala Leu Leu Val
1               5                   10                  15

Asp Ala Thr Pro Thr Thr Thr Lys Arg Ser Ala Gly Phe Val Ala Leu
            20                  25                  30

Asp Phe Ser Val Val Lys Thr Pro Lys Ala Phe Pro Val Thr Asn Gly
        35                  40                  45

Gln Glu Gly Lys Thr Ser Lys Arg Gln Ala Val Pro Val Thr Leu His
    50                  55                  60

Asn Glu Gln Val Thr Tyr Ala Ala Asp Ile Thr Val Gly Ser Asn Asn
65                  70                  75                  80
```

```
Gln Lys Leu Asn Val Ile Val Asp Thr Gly Ser Ser Asp Leu Trp Val
                85                  90                  95
Pro Asp Val Asn Val Asp Cys Gln Val Thr Tyr Ser Asp Gln Thr Ala
            100                 105                 110
Asp Phe Cys Lys Gln Lys Gly Tyr Asp Pro Ser Gly Ser Ala
        115                 120                 125
Ser Gln Asp Leu Asn Thr Pro Phe Lys Ile Gly Tyr Gly Asp Gly Ser
    130                 135                 140
Ser Ser Gln Gly Thr Leu Tyr Lys Asp Thr Val Gly Phe Gly Gly Val
145                 150                 155                 160
Ser Ile Lys Asn Gln Val Leu Ala Asp Val Asp Ser Ser Ile Asp
            165                 170                 175
Gln Gly Ile Leu Gly Val Gly Tyr Lys Thr Asn Glu Ala Gly Gly Ser
        180                 185                 190
Tyr Asp Asn Val Pro Val Thr Leu Lys Lys Gln Gly Val Ile Ala Lys
    195                 200                 205
Asn Ala Tyr Ser Leu Tyr Leu Asn Ser Pro Asp Ala Ala Thr Gly Gln
    210                 215                 220
Ile Ile Phe Gly Gly Val Asp Asn Ala Lys Tyr Ser Gly Ser Leu Ile
225                 230                 235                 240
Ala Leu Pro Val Thr Ser Asp Arg Glu Leu Arg Ile Ser Leu Gly Ser
            245                 250                 255
Val Glu Val Ser Gly Lys Thr Ile Asn Thr Asp Asn Val Asp Val Leu
        260                 265                 270
Leu Asp Ser Gly Thr Thr Ile Thr Tyr Leu Gln Gln Asp Leu Ala Asp
    275                 280                 285
Gln Ile Ile Lys Ala Phe Asn Gly Lys Leu Thr Gln Asp Ser Asn Gly
    290                 295                 300
Asn Ser Phe Tyr Glu Val Asp Cys Asn Leu Ser Gly Asp Val Val Phe
305                 310                 315                 320
Asn Phe Ser Lys Asn Ala Lys Ile Ser Val Pro Ala Ser Glu Phe Ala
            325                 330                 335
Ala Ser Leu Gln Gly Asp Asp Gly Gln Pro Tyr Asp Lys Cys Gln Leu
        340                 345                 350
Leu Phe Asp Val Asn Asp Ala Asn Ile Leu Gly Asp Asn Phe Leu Arg
    355                 360                 365
Ser Ala Tyr Ile Val Tyr Asp Leu Asp Asp Asn Glu Ile Ser Leu Ala
    370                 375                 380
Gln Val Lys Tyr Thr Ser Ala Ser Ser Ile Ser Ala Leu Thr
385                 390                 395

<210> SEQ ID NO 4
<211> LENGTH: 1194
<212> TYPE: DNA
<213> ORGANISM: Candida albicans

<400> SEQUENCE: 4 atgttttaa agaatatttt cattgctctt gctattgctt tattagtcga tgctactcca      60
acaacaacca aaagatcagc tggtttcgtt gctttagatt tcagtgttgt gaaaactcct    120
aaagcattcc cagttactaa tggtcaagaa ggtaaaactt ccaaaagaca agctgtccca    180
gtgactttac acaatgaaca agtcacttat gctgctgata ttaccgttgg atccaataat    240
caaaaactta atgttattgt tgatactgga tcatctgatt tatgggttcc tgatgttaat    300
gttgattgtc aagtcactta tagtgatcaa actgcagatt tctgtaaaca aaaggggaca    360
```

```
tatgatccaa gtggttcatc agcttcacaa gatttgaata ctccattcaa aattggttat      420
ggtgatggat cttcatctca aggtacttta tataaggata ccgttggatt tggtggtgtt      480
tcgattaaaa atcaagtttt agctgatgtt gattctactt caattgatca aggtatttta      540
ggagttggtt ataaaaccaa tgaagccggt ggtagttatg ataatgtccc tgtcacttta      600
aaaaaacaag gagtcattgc taagaatgct tattcacttt atcttaattc tccagatgct      660
gccacgggac aaataatttt cggtggggtt gataatgcta aatatagtgg ttcattaatt      720
gcattaccag ttacttctga tcgtgaatta agaattagtt tgggttcagt tgaagtttct      780
ggtaaaacca tcaatactga taatgtcgat gttcttttgg attcaggtac caccattact      840
tatttgcaac aagatcttgc tgatcaaatc attaaagctt caatggtaa attaactcaa       900 gattccaatg gtaattcatt ctatgaagtt gattgtaatt tgtcagggga tgttgtattc      960
aattttagta aaaatgctaa aatttccgtt ccagcttccg aatttgctgc ttctttacaa     1020
ggtgatgatg tcaaccata tgataaatgt caattacttt tcgatgttaa tgatgctaac      1080
attcttggtg ataacttttt gagatcagct tatattgttt atgatttgga tgataatgaa     1140
atttctttgg ctcaagtcaa atatacttct gcttccagta tttctgcctt gacc           1194
```

<210> SEQ ID NO 5
<211> LENGTH: 56
<212> TYPE: PRT
<213> ORGANISM: Candida albicans

<400> SEQUENCE: 5

```
Met Phe Leu Lys Asn Ile Phe Ile Ala Leu Ala Ile Ala Leu Leu Val
1               5                   10                  15

Asp Ala Thr Pro Thr Thr Thr Lys Arg Ser Ala Gly Phe Val Ala Leu
            20                  25                  30

Asp Phe Ser Val Val Lys Thr Pro Lys Ala Phe Pro Val Thr Asn Gly
        35                  40                  45

Gln Glu Gly Lys Thr Ser Lys Arg
    50                  55
```

<210> SEQ ID NO 6
<211> LENGTH: 168
<212> TYPE: DNA
<213> ORGANISM: Candida albicans

<400> SEQUENCE: 6

```
atgttttta agaatatttt cattgctctt gctattgctt tattagtcga tgctactcca       60
acaacaacca aaagatcagc tggtttcgtt gctttagatt tcagtgttgt gaaaactcct      120
aaagcattcc cagttactaa tggtcaagaa ggtaaaactt ccaaaaga                   168
```

<210> SEQ ID NO 7
<211> LENGTH: 342
<212> TYPE: PRT
<213> ORGANISM: Candida albicans

<400> SEQUENCE: 7

```
Gln Ala Val Pro Val Thr Leu His Asn Glu Gln Val Thr Tyr Ala Ala
1               5                   10                  15

Asp Ile Thr Val Gly Ser Asn Asn Gln Lys Leu Asn Val Ile Val Asp
            20                  25                  30

Thr Gly Ser Ser Asp Leu Trp Val Pro Asp Val Asn Val Asp Cys Gln
        35                  40                  45

Val Thr Tyr Ser Asp Gln Thr Ala Asp Phe Cys Lys Gln Lys Gly Thr
```

|  | 50 |  |  |  | 55 |  |  |  | 60 |  |  |  |
|---|---|---|---|---|---|---|---|---|---|---|---|---|

Tyr Asp Pro Ser Gly Ser Ser Ala Ser Gln Asp Leu Asn Thr Pro Phe
65                  70                  75                  80

Lys Ile Gly Tyr Gly Asp Gly Ser Ser Ser Gln Gly Thr Leu Tyr Lys
                85                  90                  95

Asp Thr Val Gly Phe Gly Gly Val Ser Ile Lys Asn Gln Val Leu Ala
            100                 105                 110

Asp Val Asp Ser Thr Ser Ile Asp Gln Gly Ile Leu Gly Val Gly Tyr
        115                 120                 125

Lys Thr Asn Glu Ala Gly Gly Ser Tyr Asp Asn Val Pro Val Thr Leu
    130                 135                 140

Lys Lys Gln Gly Val Ile Ala Lys Asn Ala Tyr Ser Leu Tyr Leu Asn
145                 150                 155                 160

Ser Pro Asp Ala Ala Thr Gly Gln Ile Ile Phe Gly Gly Val Asp Asn
                165                 170                 175

Ala Lys Tyr Ser Gly Ser Leu Ile Ala Leu Pro Val Thr Ser Asp Arg
            180                 185                 190

Glu Leu Arg Ile Ser Leu Gly Ser Val Glu Val Ser Gly Lys Thr Ile
        195                 200                 205

Asn Thr Asp Asn Val Asp Val Leu Leu Asp Ser Gly Thr Thr Ile Thr
    210                 215                 220

Tyr Leu Gln Gln Asp Leu Ala Asp Gln Ile Ile Lys Ala Phe Asn Gly
225                 230                 235                 240

Lys Leu Thr Gln Asp Ser Asn Gly Asn Ser Phe Tyr Glu Val Asp Cys
                245                 250                 255

Asn Leu Ser Gly Asp Val Val Phe Asn Phe Ser Lys Asn Ala Lys Ile
            260                 265                 270

Ser Val Pro Ala Ser Glu Phe Ala Ala Ser Leu Gln Gly Asp Asp Gly
        275                 280                 285

Gln Pro Tyr Asp Lys Cys Gln Leu Leu Phe Asp Val Asn Asp Ala Asn
    290                 295                 300

Ile Leu Gly Asp Asn Phe Leu Arg Ser Ala Tyr Ile Val Tyr Asp Leu
305                 310                 315                 320

Asp Asp Asn Glu Ile Ser Leu Ala Gln Val Lys Tyr Thr Ser Ala Ser
                325                 330                 335

Ser Ile Ser Ala Leu Thr
            340

<210> SEQ ID NO 8
<211> LENGTH: 1026
<212> TYPE: DNA
<213> ORGANISM: Candida albicans

<400> SEQUENCE: 8
caagctgtcc cagtgacttt acacaatgaa caagtcactt atgctgctga tattaccgtt      60
ggatccaata atcaaaaact taatgttatt gttgatactg gatcatctga tttatgggtt     120
cctgatgtta atgttgattg tcaagtcact tatagtgatc aaactgcaga tttctgtaaa     180
caaaagggga catatgatcc aagtggttca tcagcttcac aagatttgaa tactccattc     240
aaaattggtt atggtgatgg atcttcatct caaggtactt tatataagga taccgttgga     300
tttggtggtg tttcgattaa aaatcaagtt ttagctgatg ttgattctac ttcaattgat     360
caaggtattt taggagttgg ttataaaacc aatgaagccg gtggtagtta tgataatgtc     420
cctgtcactt taaaaaaaca aggagtcatt gctaagaatg cttattccact ttatcttaat     480

-continued

```
tctccagatg ctgccacggg acaaataatt ttcggtgggg ttgataatgc taaatatagt    540
ggttcattaa ttgcattacc agttacttct gatcgtgaat taagaattag tttgggttca    600
gttgaagttt ctggtaaaac catcaatact gataatgtcg atgttctttt ggattcaggt    660
accaccatta cttatttgca acaagatctt gctgatcaaa tcattaaagc tttcaatggt    720
aaattaactc aagattccaa tggtaattca ttctatgaag ttgattgtaa tttgtcaggg    780
gatgttgtat tcaattttag taaaaatgct aaaatttccg ttccagcttc cgaatttgct    840
gcttctttac aaggtgatga tggtcaacca tatgataaat gtcaattact tttcgatgtt    900
aatgatgcta acattcttgg tgataacttt ttgagatcag cttatattgt ttatgatttg    960
gatgataatg aaatttcttt ggctcaagtc aaatatactt ctgcttccag tatttctgcc   1020
ttgacc                                                              1026

<210> SEQ ID NO 9
<211> LENGTH: 34
<212> TYPE: DNA
<213> ORGANISM: Candida albicans

<400> SEQUENCE: 9 ggggatcca tcttttaaa gaatattttc attg                                   34

<210> SEQ ID NO 10
<211> LENGTH: 35
<212> TYPE: DNA
<213> ORGANISM: Candida albicans

<400> SEQUENCE: 10
cctaagcttg gtcaaggcag aaatactgga agcag                                35
```